US012508045B2

(12) United States Patent
Bartinelli, Jr. et al.

(10) Patent No.: US 12,508,045 B2
(45) Date of Patent: Dec. 30, 2025

(54) ROBOTIC SURGICAL SYSTEM WITH KNIFE DRIVE MECHANISM

(71) Applicant: Cilag GmbH International, Zug (CH)

(72) Inventors: William S. Bartinelli, Jr., West Chester, OH (US); Matthew T. Stone, Mason, OH (US); Benjamin D. Dickerson, San Francisco, CA (US)

(73) Assignee: Cilag GmbH International, Zug (CH)

( * ) Notice: Subject to any disclaimer, the term of this patent is extended or adjusted under 35 U.S.C. 154(b) by 394 days.

(21) Appl. No.: 18/092,575

(22) Filed: Jan. 3, 2023

(65) Prior Publication Data

US 2024/0215999 A1 Jul. 4, 2024

(51) Int. Cl.

| | |
|---|---|
| ***A61B 17/285*** | (2006.01) |
| ***A61B 34/37*** | (2016.01) |
| ***B66D 1/74*** | (2006.01) |

(52) U.S. Cl.

CPC ............ *A61B 17/285* (2013.01); *A61B 34/37* (2016.02); *B66D 1/7405* (2013.01); *B66D 1/7484* (2013.01); *B66D 1/7489* (2013.01)

(58) Field of Classification Search

CPC ..... A61B 17/285; A61B 34/37; A61B 17/068; A61B 17/072; A61B 17/28; A61B 17/320092; B66D 1/7405; B66D 1/7484; B66D 1/7489

See application file for complete search history.

(56) References Cited

U.S. PATENT DOCUMENTS

| | | | |
|---|---|---|---|
| 7,354,440 B2 | 4/2008 | Truckai et al. | |
| 7,381,209 B2 | 6/2008 | Truckai et al. | |
| 8,663,220 B2 | 3/2014 | Wiener et al. | |
| 9,949,785 B2 | 4/2018 | Price et al. | |
| 2022/0226048 A1* | 7/2022 | Beckman ......... | A61B 17/07207 |
| 2022/0226056 A1* | 7/2022 | Beckman ............... | B25J 9/1035 |

* cited by examiner

*Primary Examiner* — Mohamed G Gabr
*Assistant Examiner* — Khoa Tan Le
(74) *Attorney, Agent, or Firm* — Frost Brown Todd LLP

(57) ABSTRACT

An apparatus includes an end effector, a shaft assembly extending proximally from the end effector, an instrument base, and a knife driving assembly. The end effector includes a pair of jaws and a knife member capable of actuating between a proximal and distal position. The knife driving assembly can actuate the knife member between the proximal and distal position. The knife driving assembly includes a cable and a knife drive input assembly coupled only to a first drive input. The knife driven assembly is capable of rotating in first and second angular directions. The cable terminates into a first end and a second end, which are both attached to the knife drive input assembly. A portion of the cable is attached to the knife member. Rotation of the knife drive input assembly in the first angular direction drives the knife member distally. Rotation of the knife drive input assembly in the second angular direction drives the knife member proximally.

20 Claims, 33 Drawing Sheets

ROBOTIC SURGICAL SYSTEM WITH KNIFE DRIVE MECHANISM

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically assisted surgery. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a tissue grasper, a needle driver, an electrosurgical cautery probes, etc. Each of these structures performs functions for the surgeon, for example, cutting tissue, coagulating tissue, holding or driving a needle, grasping a blood vessel, dissecting tissue, or cauterizing tissue.

Some instruments are operable to seal tissue by applying radiofrequency (RF) electrosurgical energy to the tissue. Examples of such devices and related concepts are disclosed in U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein; and U.S. Pat. No. 8,663,220, entitled "Ultrasonic Surgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
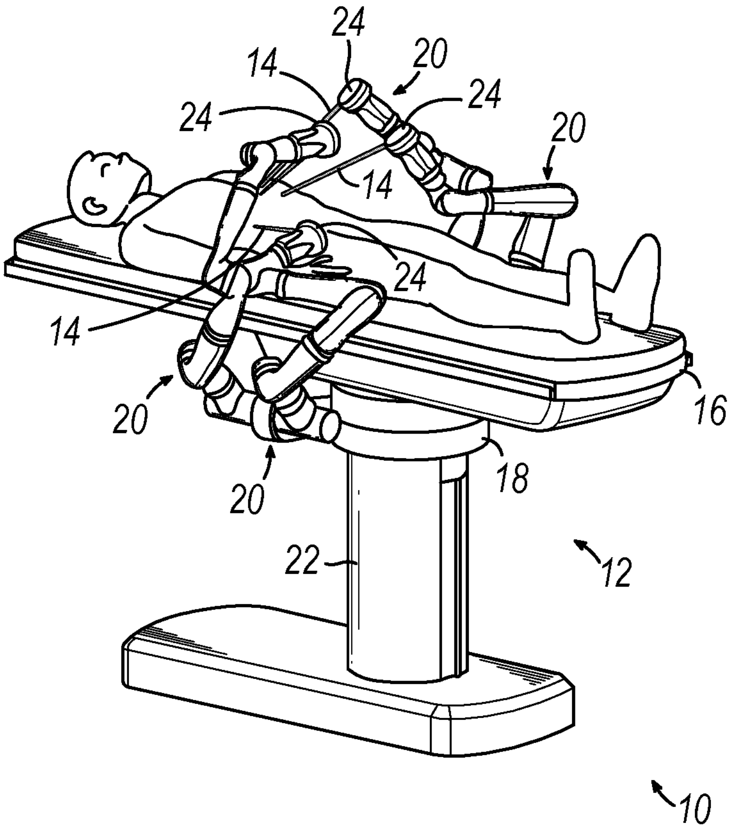
FIG. 1 depicts a perspective view of a first example of a table-based robotic system configured for a laparoscopic procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "front," "rear," "clockwise," "counterclockwise," "longitudinal," and "transverse" also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

In addition to performing the breadth of procedures, the robotically-enabled medical system may provide additional benefits, such as enhanced imaging and guidance to assist the medical professional. Additionally, the robotically-enabled medical system may provide the medical professional with the ability to perform the procedure from an ergonomic position without the need for awkward arm motions and positions. Still further, the robotically-enabled medical system may provide the medical professional with the ability to perform the procedure with improved ease of use such that one or more of the instruments of the robotically-enabled medical system may be controlled by a single operator.

I. Illustrative Robotically-Enabled Medical System

FIG. 1 shows an Illustrative robotically-enabled medical system, including a first example of a table-based robotic system (10). Table-based robotic system (10) of the present example includes a table system (12) operatively connected to an instrument for a diagnostic and/or therapeutic procedure in the course of treating a patient. Such procedures may include, but are not limited, to bronchoscopy, ureteroscopy, a vascular procedure, and a laparoscopic procedure. To this end, the instrument illustrated in the present example is an RF energy enabled surgical instrument (14) configured for a laparoscopic procedure, although it will be appreciated that any instrument for treating a patient may be similarly used.

At least part of table-based robotic system (10) may be constructed and operable in accordance with at least some of the teachings of any of the various patents, patent application publications, and patent applications that are cited herein. As described therein and as will be described in greater detail below, RF energy surgical instrument (14) is operable to sever tissue and/or apply RF therapeutic energy to tissue. While one or more examples incorporates various RF electrosurgical energy features, such as RF energy surgical instrument (14), the invention is not intended to be unnecessarily limited to the RF features described herein.

A. First Illustrative Table-Based Robotic System

With respect to FIG. 1, table-based robotic system (10) includes table system (12) having a platform, such as a table (16), with a plurality of carriages (18) which may also be referred to herein as "arm supports," respectively supporting the deployment of a plurality of robotic arms (20). Table-based robotic system (10) further includes a support structure, such as a column (22), for supporting table (16) over the floor. Table (16) may also be configured to tilt to a desired angle during use, such as during laparoscopic procedures. Each robotic arm (20) includes an instrument driver (24) configured to removably connect to and manipulate RF energy surgical instrument (14) for use. In alternative examples, instrument drivers (24) may be collectively positioned in a linear arrangement to support the instrument extending therebetween along a "virtual rail" that may be repositioned in space by manipulating the one or more robotic arms (20) into one or more angles and/or positions. In practice, a C-arm (not shown) may be positioned over the patient for providing fluoroscopic imaging.

In the present example, column (22) includes carriages (18) arranged in a ring-shaped form to respectively support one or more robotic arms (20) for use. Carriages (18) may translate along column (22) and/or rotate about column (22) as driven by a mechanical motor (not shown) positioned within column (22) in order to provide robotic arms (20) with access to multiples sides of table (16), such as, for example, both sides of the patient. Rotation and translation of carriages (18) allows for alignment of instruments, such as RF energy surgical instrument (14) into different access points on the patient. In alternative examples, such as those discussed below in greater detail, table-based robotic system (10) may include a patient table or bed with adjustable arm supports including a bar (26) (see FIG. 2) extending alongside. One or more robotic arms (20) (e.g., via a shoulder with an elbow joint) may be attached to carriages (18), which are vertically adjustable so as to be stowed compactly beneath the patient table or bed, and subsequently raised during use.

Table-based robotic system (10) may also include a tower (not shown) that divides the functionality of table-based robotic system (10) between table (16) and the tower to reduce the form factor and bulk of table (16). To this end, the tower may provide a variety of support functionalities to table (16), such as processing, computing, and control capabilities, power, fluidics, and/or optical and sensor processing. The tower may also be movable so as to be positioned away from the patient to improve medical professional access and de-clutter the operating room. The tower may also include a master controller or console that provides both a user interface for operator input, such as keyboard and/or pendant, as well as a display screen, including a touchscreen, for pre-operative and intra-operative information, including, but not limited to, real-time imaging, navigation, and tracking information. In one example, the tower may include gas tanks to be used for insufflation.

B. Second Illustrative Table-Based Robotic System

Figure 2:
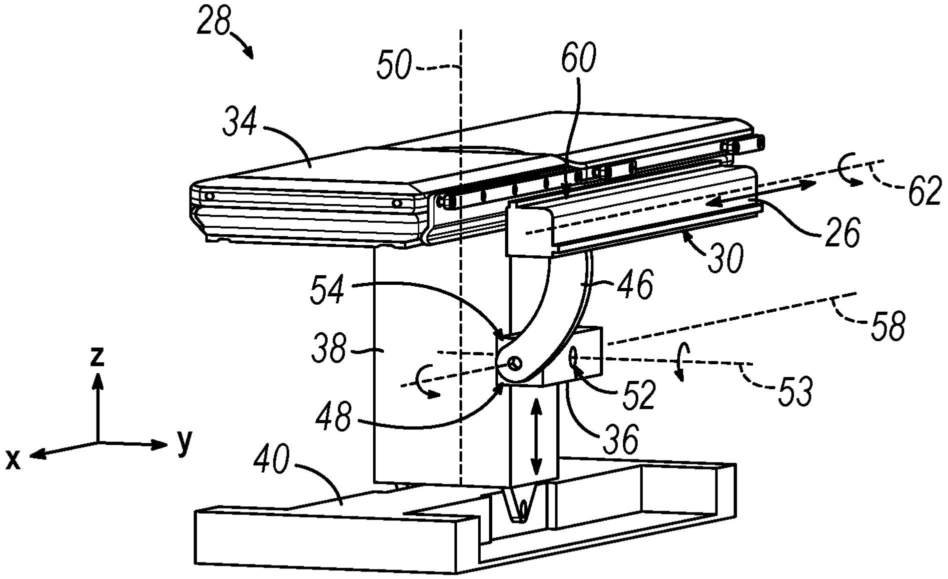
FIG. 2 depicts a perspective view of a second example of a table-based robotic system.
Figure 3:
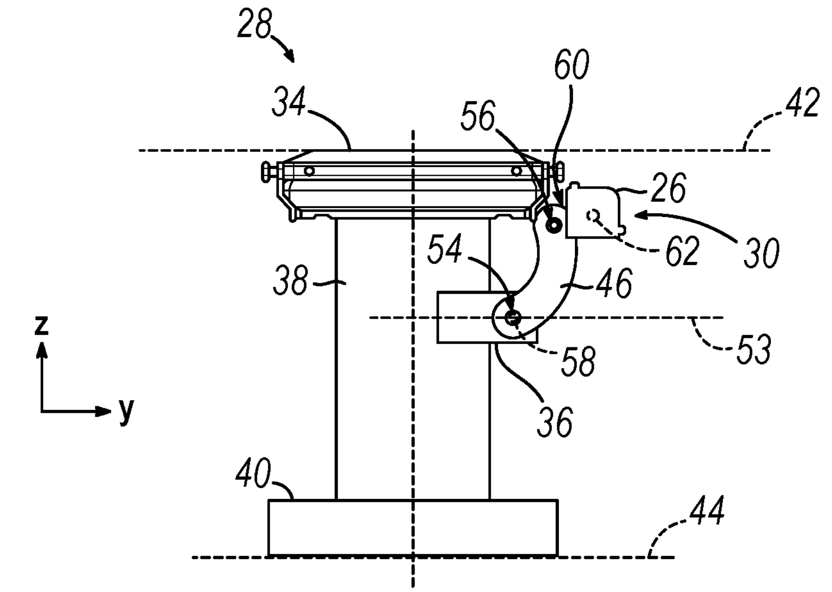
FIG. 3 depicts an end elevational view of the table-based robotic system of FIG. 2.
Figure 4:
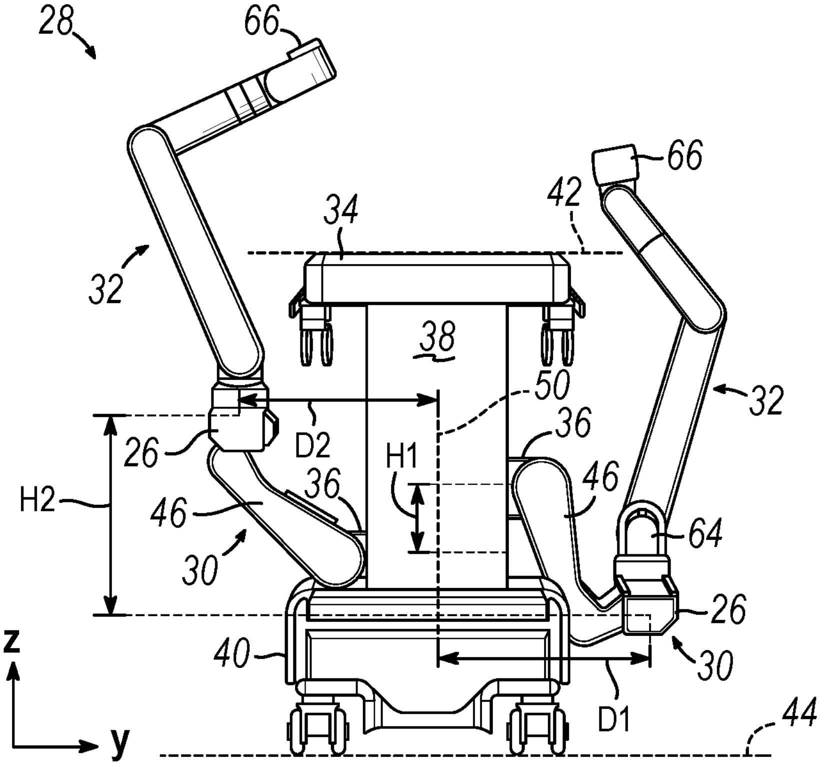
FIG. 4 depicts the end elevational view of the table-based robotic system of FIG. 3 including a pair of Illustrative robotic arms.

As discussed briefly above, a second Illustrative table-based robotic system (28) includes one or more adjustable arm supports (30) including bars (26) configured to support one or more robotic arms (32) relative to a table (34) as shown in FIGS. 2-4. In the present example, a single and a pair of adjustable arm supports (30) are shown, though additional arm supports (30) may be provided about table (34). Adjustable arm support (30) is configured to selectively move relative to table (34) so as to alter the position of adjustable arm support (30) and/or any robotic arms (32) mounted thereto relative to table (34) as desired. Such adjustable arm supports (30) provide high versatility to table-based robotic system (28), including the ability to easily stow one or more adjustable arm supports (30) with robotic arms (32) beneath table (34).

Each adjustable arm support (30) provides several degrees of freedom, including lift, lateral translation, tilt, etc. In the present example shown in FIGS. 2-4, arm support (30) is configured with four degrees of freedom, which are illustrated with arrows. A first degree of freedom allows adjustable arm support (30) to move in the z-direction ("Z-lift"). For example, adjustable arm support (30) includes a vertical carriage (36) configured to move up or down along or relative to a column (38) and a base (40) supporting table (34). A second degree of freedom allows adjustable arm support (30) to tilt about an axis extending in the y-direction. For example, adjustable arm support (30) includes a rotary joint, which allows adjustable arm support (30) to align the bed in a Trendelenburg position. A third degree of freedom allows adjustable arm support (30) to "pivot up" about an axis extending in the x-direction, which may be useful to adjust a distance between a side of table (34) and adjustable arm support (30). A fourth degree of freedom allows translation of adjustable arm support (30) along a longitudinal length of table (34), which extends along the x-direction. Base (40) and column (38) support table (34) relative to a support surface, which is shown along a support axis (42) above a floor axis (44) and in the present example. While the present example shows adjustable arm support (30) mounted to column (38), arm support (30) may alternatively be mounted to table (34) or base (40).

As shown in the present example, adjustable arm support (30) includes vertical carriage (36), a bar connector (46), and bar (26). To this end, vertical carriage (36) attaches to column (38) by a first joint (48), which allows vertical carriage (36) to move relative to column (38) (e.g., such as up and down a first, vertical axis (50) extending in the z-direction). First joint (48) provides the first degree of freedom ("Z-lift") to adjustable arm support (30). Adjustable arm support (30) further includes a second joint (52), which provides the second degree of freedom (tilt) for adjustable arm support (30) to pivot about a second axis (53) extending in the y-direction. Adjustable arm support (30) also includes a third joint (54), which provides the third degree of freedom ("pivot up") for adjustable arm support (30) about a third axis (58) extending in the x-direction. Furthermore, an additional joint (56) mechanically constrains third joint (54) to maintain a desired orientation of bar (26) as bar connector (46) rotates about third axis (58). Adjustable arm support (30) includes a fourth joint (60) to provide a fourth degree of freedom (translation) for adjustable arm support (30) along a fourth axis (62) extending in the x-direction.

With respect to FIG. 4, table-based robotic system (28) is shown with two adjustable arm supports (30) mounted on opposite sides of table (34). A first robotic arm (32) is attached to one such bar (26) of first adjustable arm support (30). First robotic arm (32) includes a base (64) attached to bar (26). Similarly, second robotic arm (32) includes base (64) attached to other bar (26). Distal ends of first and second robotic arms (32) respectively include instrument drivers (66), which are configured to attach to one or more instruments such as those discussed below in greater detail.

In one example, one or more robotic arms (32) has seven or more degrees of freedom. In another example, one or more robotic arms (32) has eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base (64) (1-degree of freedom including translation). In one example, the insertion degree of freedom is provided by robotic arm (32), while in another example, such as RF energy surgical instrument (14) (see FIG. 6A), the instrument includes an instrument-based insertion architecture.

Figure 5:
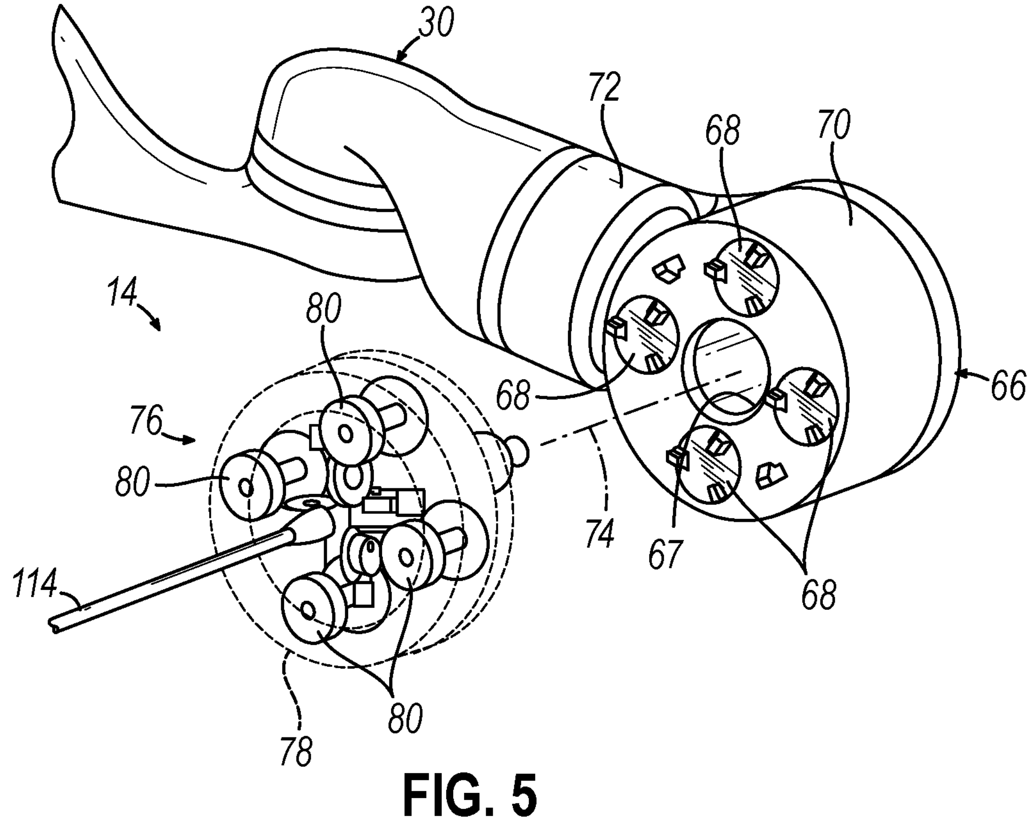
FIG. 5 depicts a partially exploded perspective view of the robotic arm of FIG. 4 having an instrument driver and a first Illustrative surgical instrument.

FIG. 5 shows one example of instrument driver (66) in greater detail with RF energy surgical instrument (14) removed therefrom. Given the present instrument-based insertion architecture shown with reference to surgical instrument (14), instrument driver (66) further includes a clearance bore (67) extending entirely therethrough so as to movably receive a portion of surgical instrument (14) as discussed below in greater detail. Instrument driver (66) may also be referred to herein as an "instrument drive mechanism," an "instrument device manipulator," or an "advanced device manipulator" (ADM). Instruments may be designed to be detached, removed, and interchanged from instrument driver (66) for individual sterilization or disposal by the medical professional or associated staff. In some scenarios, instrument drivers (66) may be draped for protection and thus may not need to be changed or sterilized.

Each instrument driver (66) operates independently of other instrument drivers (66) and includes a plurality of rotary drive outputs (68), such as four drive outputs (68), also independently driven relative to each other for directing operation of surgical instrument (14). Instrument driver (66) and surgical instrument (14) of the present example are aligned such that the axes of each drive output (68) are parallel to the longitudinal axis of surgical instrument (14). In use, control circuitry (not shown) receives a control signal, transmits motor signals to desired motors (not shown), compares resulting motor speed as measured by respective encoders (not shown) with desired speeds, and modulates motor signals to generate desired torque at one or more drive outputs (68).

In the present example, instrument driver (66) is circular with respective drive outputs (68) housed in a rotational assembly (70). In response to torque, rotational assembly (70) rotates along a circular bearing (not shown) that connects rotational assembly (70) to a non-rotational portion (72) of instrument driver (66). Power and controls signals may be communicated from non-rotational portion (72) of instrument driver (66) to rotational assembly (70) through electrical contacts therebetween, such as a brushed slip ring connection (not shown). In one example, rotational assembly (70) may be responsive to a separate drive output (not shown) integrated into non-rotatable portion (72), and thus not in parallel to the other drive outputs (68). In any case, rotational assembly (70) allows instrument driver (66) to rotate rotational assembly (70) and drive outputs (68) in conjunction with surgical instrument (14) as a single unit around an instrument driver axis (74).

Any systems described herein, including table-based robotic system (28), may further include an input controller (not shown) for manipulating one or more instruments. In some embodiments, the input controller (not shown) may be coupled (e.g., communicatively, electronically, electrically, wirelessly and/or mechanically) with an instrument such that manipulation of the input controller (not shown) causes a corresponding manipulation of the instrument e.g., via master slave control. In one example, one or more load cells (not shown) may be positioned in the input controller such that portions of the input controller (not shown) are capable of operating under admittance control, thereby advantageously reducing the perceived inertia of the controller while in use.

In addition, any systems described herein, including table-based robotic system (28) may provide for non-radiation-based navigational and localization means to reduce exposure to radiation and reduce the amount of equipment within the operating room. As used herein, the term "localization" may refer to determining and/or monitoring the position of objects in a reference coordinate system. Technologies such as pre-operative mapping, computer vision, real-time electromagnetic sensor (EM) tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

C. First Illustrative RF Energy Surgical Instrument

Figure 6A:
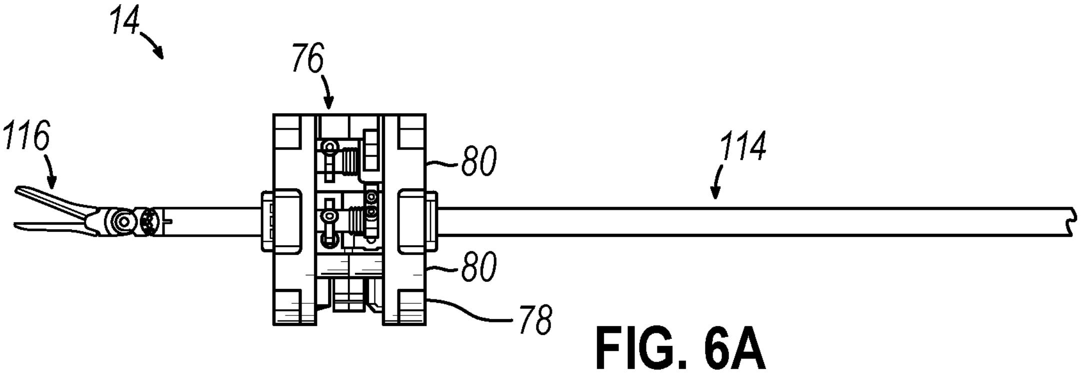
FIG. 6A depicts a side elevational view of the surgical instrument of FIG. 5 in a retracted position.
Figure 6B:
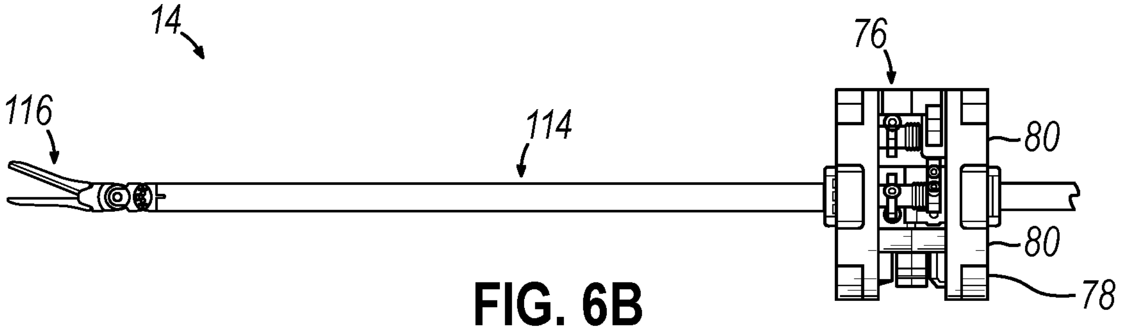
FIG. 6B depicts the side elevational view the surgical instrument similar to FIG. 6A, but in an extended position.

With respect to FIGS. 5-6B and in cooperation with instrument driver (66) discussed above, surgical instrument (14) includes an elongated shaft assembly (114) and an instrument base (76) with an attachment interface (78) having a plurality of drive inputs (80) configured to respectively couple with corresponding drive outputs (68). Shaft assembly (114) of RF energy surgical instrument (14) extends from a center of base (76) with an axis substantially parallel to the axes of the drive inputs (80) as discussed briefly above. With shaft assembly (114) positioned at the center of base (76), shaft assembly (114) is coaxial with instrument driver axis (74) when attached and movably received in clearance bore (67). Thus, rotation of rotational assembly (70) causes shaft assembly (114) of RF energy surgical instrument (14) to rotate about its own longitudinal axis while clearance bore (67) provides space for translation of shaft assembly (114) during use.

To this end, FIGS. 6A-6B show surgical instrument (14) having the instrument-based insertion architecture as discussed briefly above. Surgical instrument (14) includes elongated shaft assembly (114), an end effector (116) connected to and extending distally from shaft assembly (114), and instrument base (76) coupled to shaft assembly (114). Notably, insertion of shaft assembly (114) is grounded at instrument base (76) such that end effector (116) is configured to selectively move longitudinally from a retracted position to an extended position, vice versa, and any desired longitudinal position therebetween. As used herein, the retracted position is shown in FIG. 6A and places end effector (116) relatively close and proximally toward instrument base (76), whereas the extended position is shown in FIG. 6B and places end effector (116) relatively far and distally away from instrument base (76). Insertion into and withdrawal of end effector (116) relative to the patient may thus be facilitated by RF energy surgical instrument (14), although it will be appreciated that such insertion into and withdrawal may also occur via robotic arms (see FIG. 5) in one or more examples.

While various features configured to facilitate movement between end effector (116) and drive inputs (80) are described herein, such features may additionally or alternatively include pulleys, cables, carriers, such as a kinetic articulating rotating tool (KART), and/or other structures configured to communicate movement along shaft assembly (114). Moreover, while instrument base (76) is configured to operatively connect to instrument driver (66) for driving various features of shaft assembly (114) and/or end effector (116) as discussed below in greater detail, it will be appreciated that alternative examples may operatively connect shaft assembly (114) and/or end effector (116) to an alternative handle assembly (not shown). Such handle assembly (not shown) may include a pistol grip (not shown) in one example, configured to be directly gripped and manipulated by the medical professional for driving various features of shaft assembly (114) and/or end effector (116). The invention is thus not intended to be unnecessarily limited to use with instrument driver (66).

Turning to FIGS. 7A-8B, end effector (116) includes a first jaw (120) having a first electrode surface (121), a second jaw (122) having a second electrode surface (123), and a knife member (125) slidably disposed within a knife channel (124) cooperatively defined by first jaw (120) and second jaw (122). As will be described in greater detail below, end effector (116) of the current example in configured to grasp tissue with jaws (120, 122), seal tissue by applying bipolar RF energy to tissue via electrodes (121, 123), and sever tissue utilized knife member (125). In the current example, end effector (116) is suitably coupled to drive inputs (80) via cables and pulleys in order to suitably actuate components of end effector (116) in accordance with the description herein.

Figure 7A:
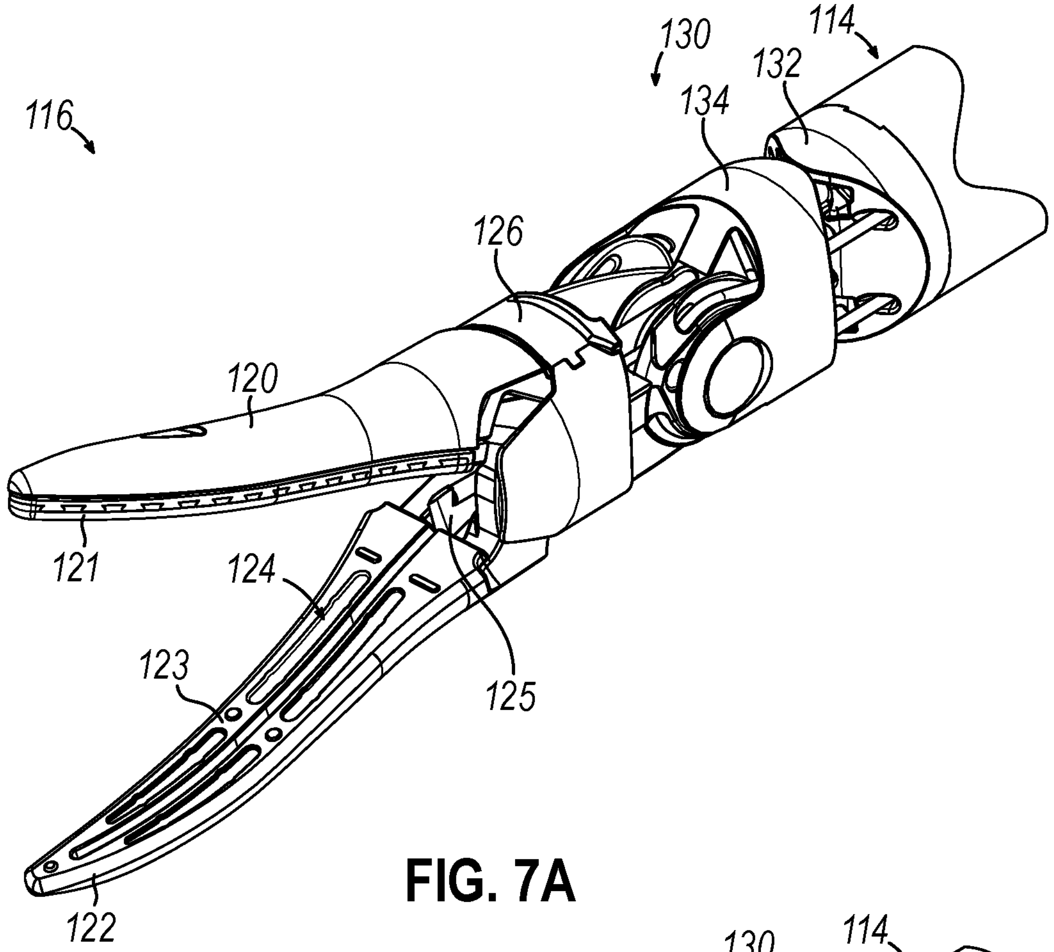
FIG. 7A depicts a perspective view of an end effector of the surgical instrument of FIG. 5, with jaws of the end effector in an open position.
Figure 7B:
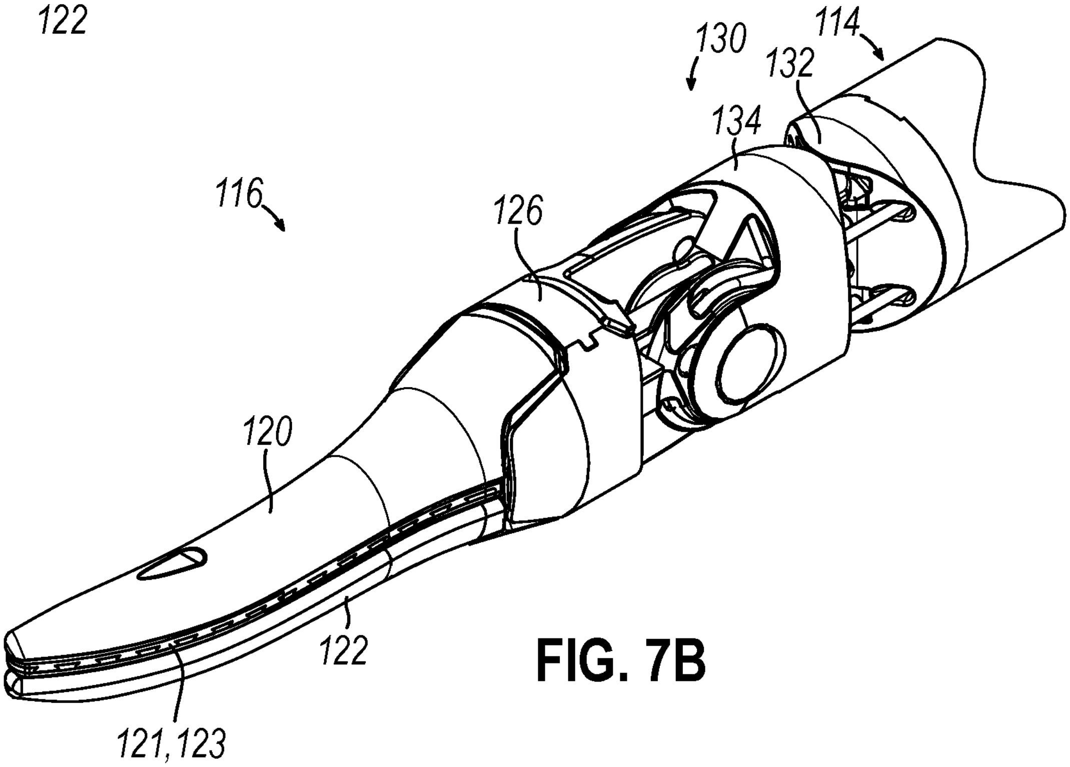
FIG. 7B depicts a perspective view of the end effector of FIG. 7A, with the jaws of FIG. 7A in a closed position.

As shown between FIGS. 7A-7B, first jaw (120) and second jaw (122) are pivotally coupled to each other such that jaws (120, 122) may actuate between an open position and a closed position in order to grasp tissue. In the current example, jaws (120, 122) are operatively attached to a clevis assembly (126) configured to translate to thereby pivot jaws (120, 122) between the open position and the closed position. While a clevis assembly (126) is utilized in the current example, any other suitable structures may be utilized in order to drive jaws (120, 122) between the open and closed positions as would be apparent to one skilled in the art in view of the teachings herein.

Figure 7C:
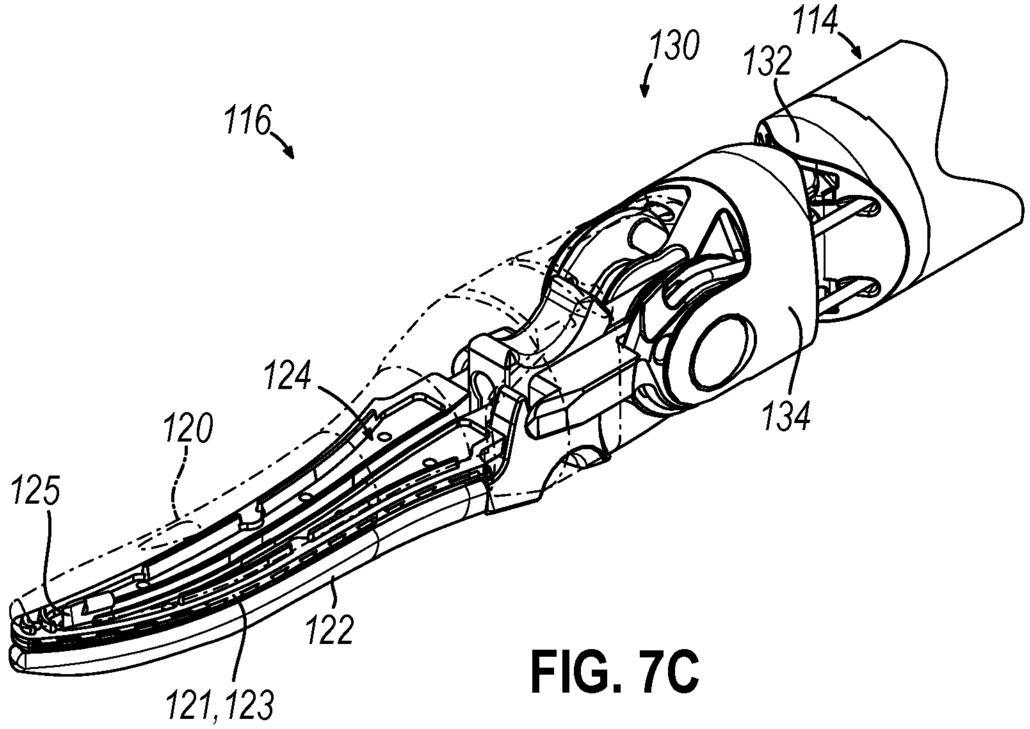
FIG. 7C depicts a perspective view of the end effector of FIG. 7A, with the jaws of FIG. 7A in a closed position and a knife member in the extended position, with one jaw shown in phantom.

As best shown between FIGS. 7B-7C, while jaws (120, 122) are in the closed position, knife member (125) may be driven distally along the path defined by knife channel (124) from a proximal position (as illustrated in FIG. 7A) and a distal position in order to sever tissue grasped by jaws (120, 122). Once knife member (125) reaches the distal position within knife channel (124) in order to suitably sever tissue, knife member (125) may then be retracted within knife channel (124) back into the proximal position. In instances where a cable is used to actuate knife member (125) within knife channel (124) between the proximal and distal positions, such a cable may be attached to a first drive input (80) dedicated to distally actuating knife member (125); while the cable may also be attached to a second drive input (80) dedicated to proximally actuating knife member (125).

Electrode surfaces (121, 123) may be activated during any suitable time at which jaws (120, 122) interact with tissue in order to apply bipolar RF energy to tissue. For example, electrode surfaces (121, 123) may be activated after knife member (125) severs tissue in order to seal the recently severed tissue grasped between jaws (120, 122). As another illustrative example, electrode surfaces (121, 123) may be activated prior to knife member (125) serving tissue. As yet another illustrative example, electrode surface (121, 123) may be activated in order to cauterize tissue without cutting tissue.

In the current example, electrode surface (121) is an electrode body attached on the underside of jaw (120); while jaw (122) is formed from a suitable material in order to act as electrode surface (123). For example, jaw (122) may be formed of a metal material and be in connection with a ground wire; while electrode body forming electrode surface (121) is attached the underside of jaw (120) and in communication with a hot wire. Once suitably activated, RF energy may be transmitted between electrode surfaces (121, 123) in order to further transmit such RF energy through tissue.

Electrode surfaces (121, 123) may have any suitable configuration as would be apparent to one skilled in the art in view of the teachings herein. While in the current example, electrode surfaces (121, 123) are configured to deliver bipolar RF energy to tissue, it should be understood that end effector (116) may be configured to deliver any other suitable type of therapeutic energy to tissue as would be apparent to one skilled in the art in view of the teachings herein.

Figure 8A:
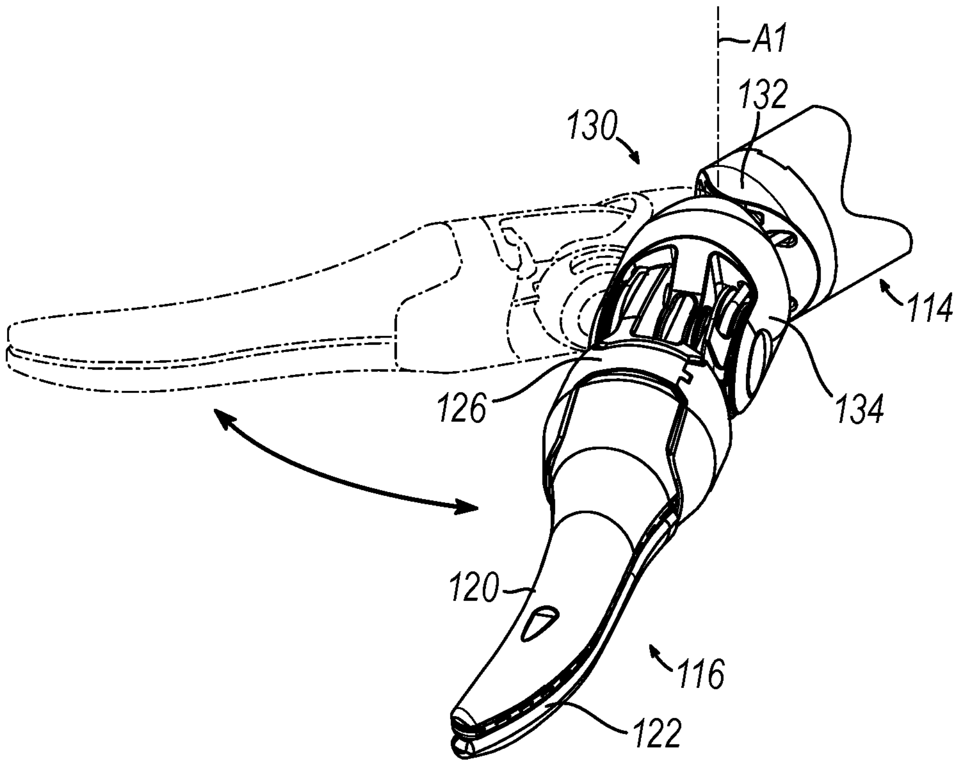
FIG. 8A depicts a perspective view of the end effector of FIG. 7A in a first articulated position.
Figure 8B:
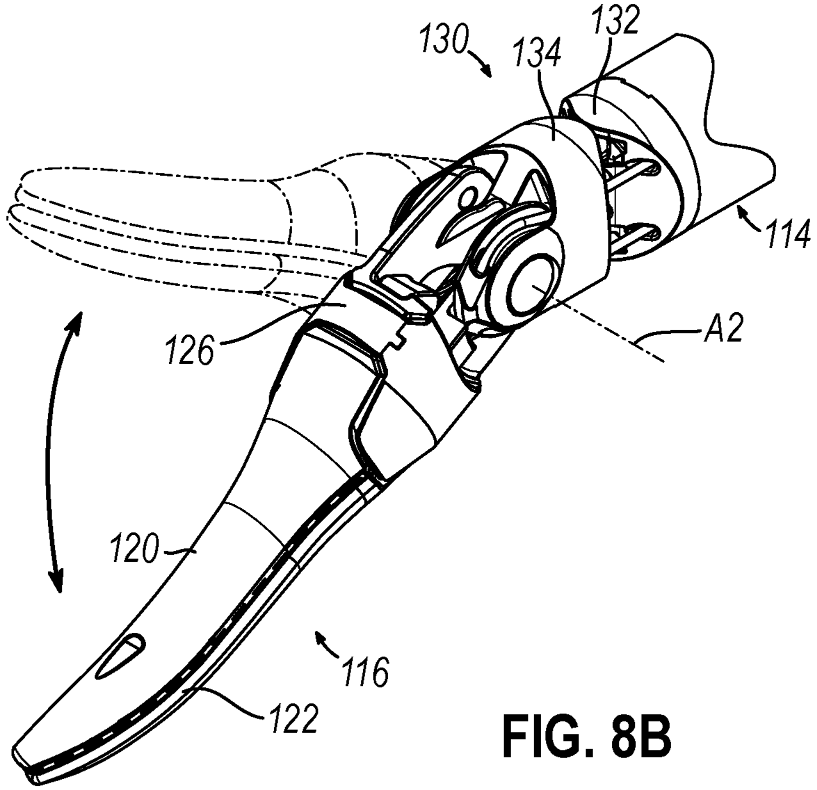
FIG. 8B depicts a perspective view of the end effector of FIG. 7A in a second articulated position.

Turning to FIGS. 8A-8B, end effector (116) also includes an articulation assembly (130) configured to deflect jaws (120, 122) relative to the longitudinal axis of shaft assembly (114). In the current example, articulation assembly (130) include a proximal camming body (132) associated with a distal end of shaft assembly (114) and a distal camming body (134) associated with a proximal end of end effector (116). Camming bodies (132, 134) are configured to engage each other as jaws (120, 122) are articulated about a first axis (A1), as shown in FIG. 8A. In some instances, articulation assembly (130) may be configured to pivot both jaws (120, 122) about a second axis (A2), as shown in FIG. 8B.

D. Illustrative Instrument Having Instrument Base with Elongated Splines

Figure 11A:
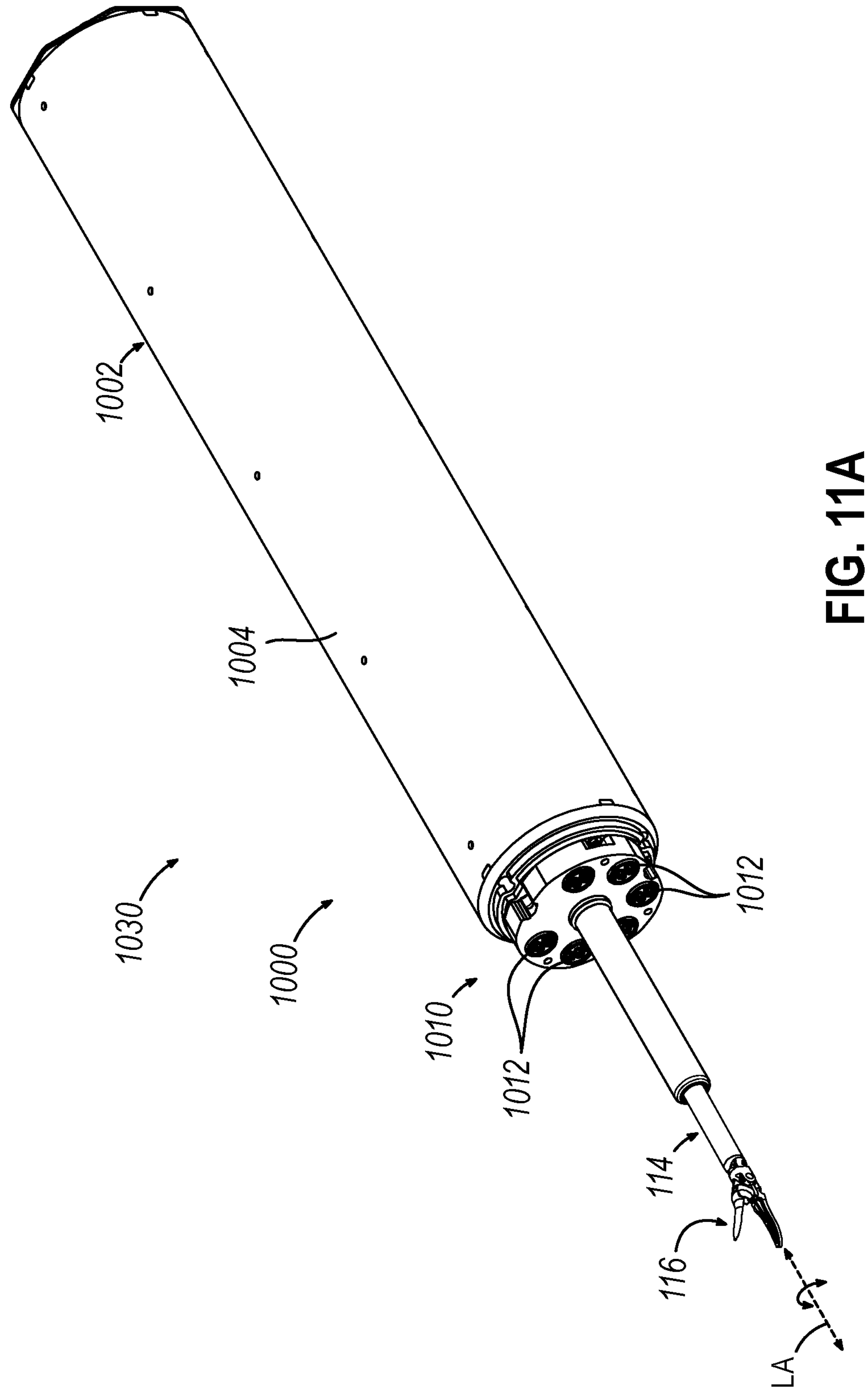
FIG. 11A depicts a perspective view of the instrument base of FIG. 9, an exemplary shaft assembly, and an exemplary end effector coupled together to form an exemplary ultrasonic surgical instrument configured to couple with an exemplary robotic arm, where the shaft assembly and end effector are in a proximal position.
Figure 11B:
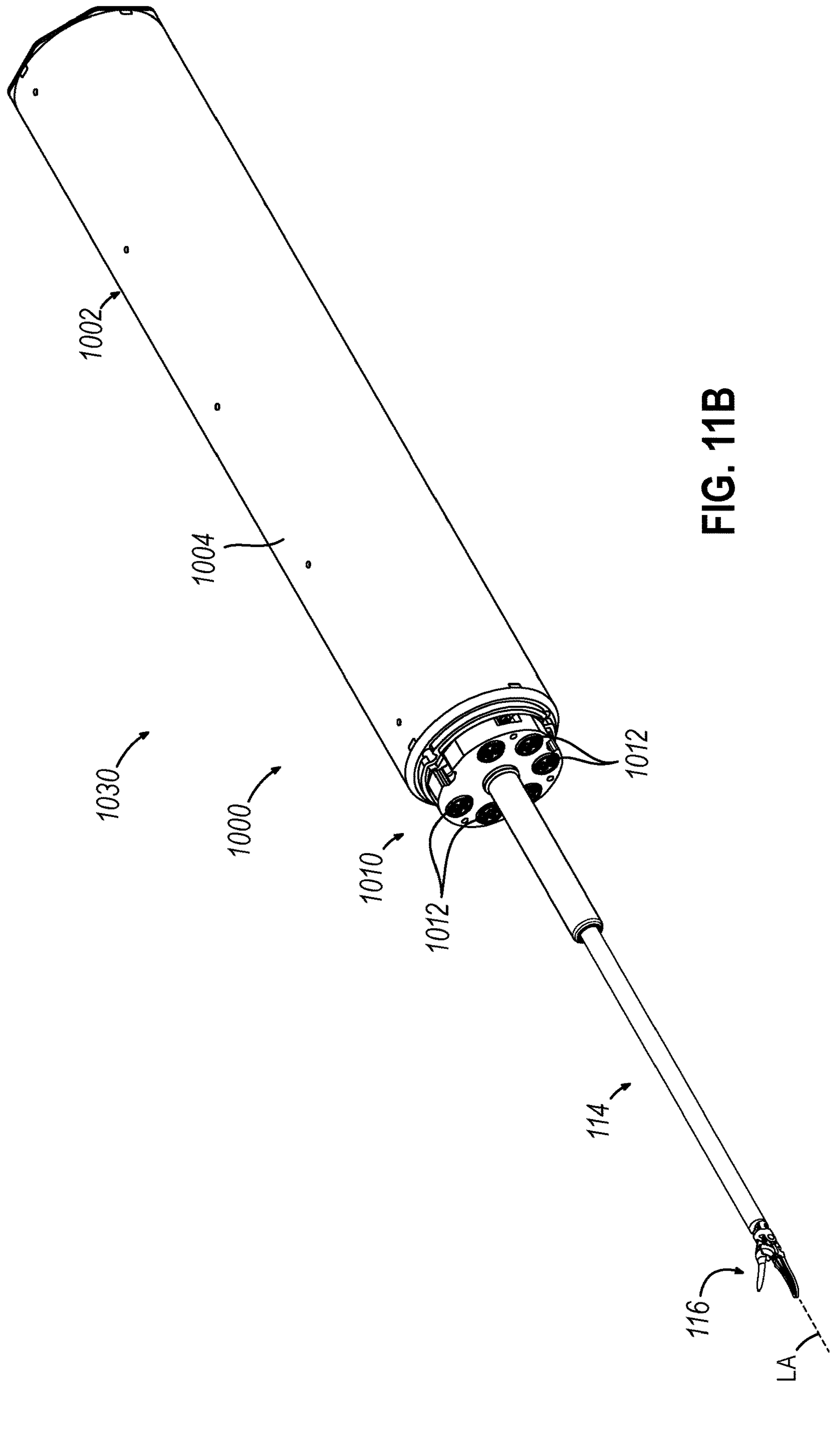
FIG. 11B depicts the ultrasonic surgical instrument of FIG. 11A, where the shaft assembly and the end effector are in a distal position.

FIGS. 11A-11B show an alternative RF energy surgical instrument (1030) that may be incorporated into an Illustrative robotic arm substantially similar to robotic arm (20, 32) described above, with any differences elaborated below. Therefore, RF energy surgical instrument (1030) may be substantially similar to surgical instrument (14) described above, except as otherwise described below.

RF energy surgical instrument (1030) includes an instrument base (1000), shaft assembly (114) partially housed within, and extending distally from, instrument base (1000), and an end effector (116) extending distally from shaft assembly (114). Instrument base (1000) instrument base (76) described above, with differences elaborated below.

Figure 9:
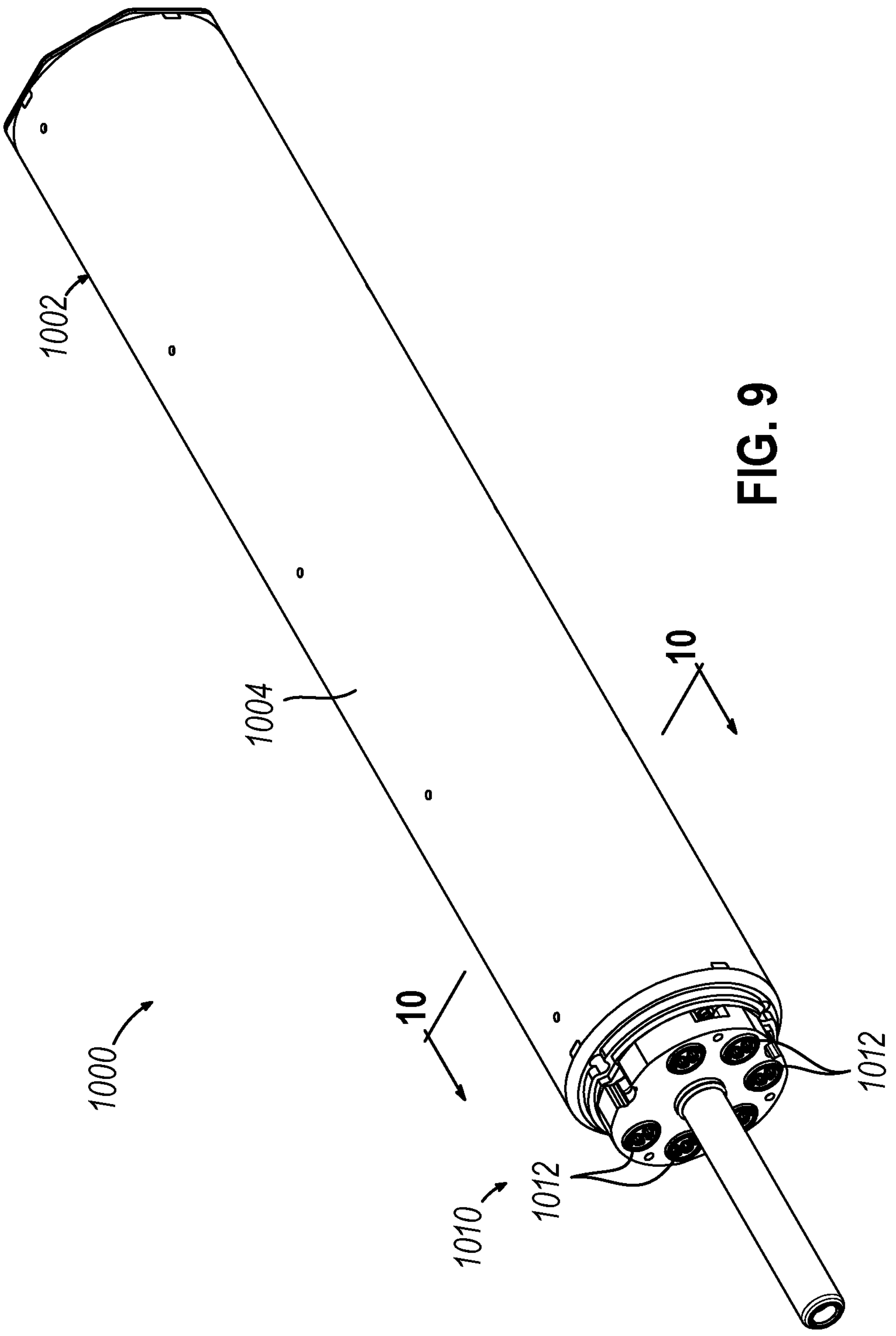
FIG. 9 depicts a perspective view of an exemplary instrument base that may be configured to couple with an exemplary robotic arm.
Figure 10:
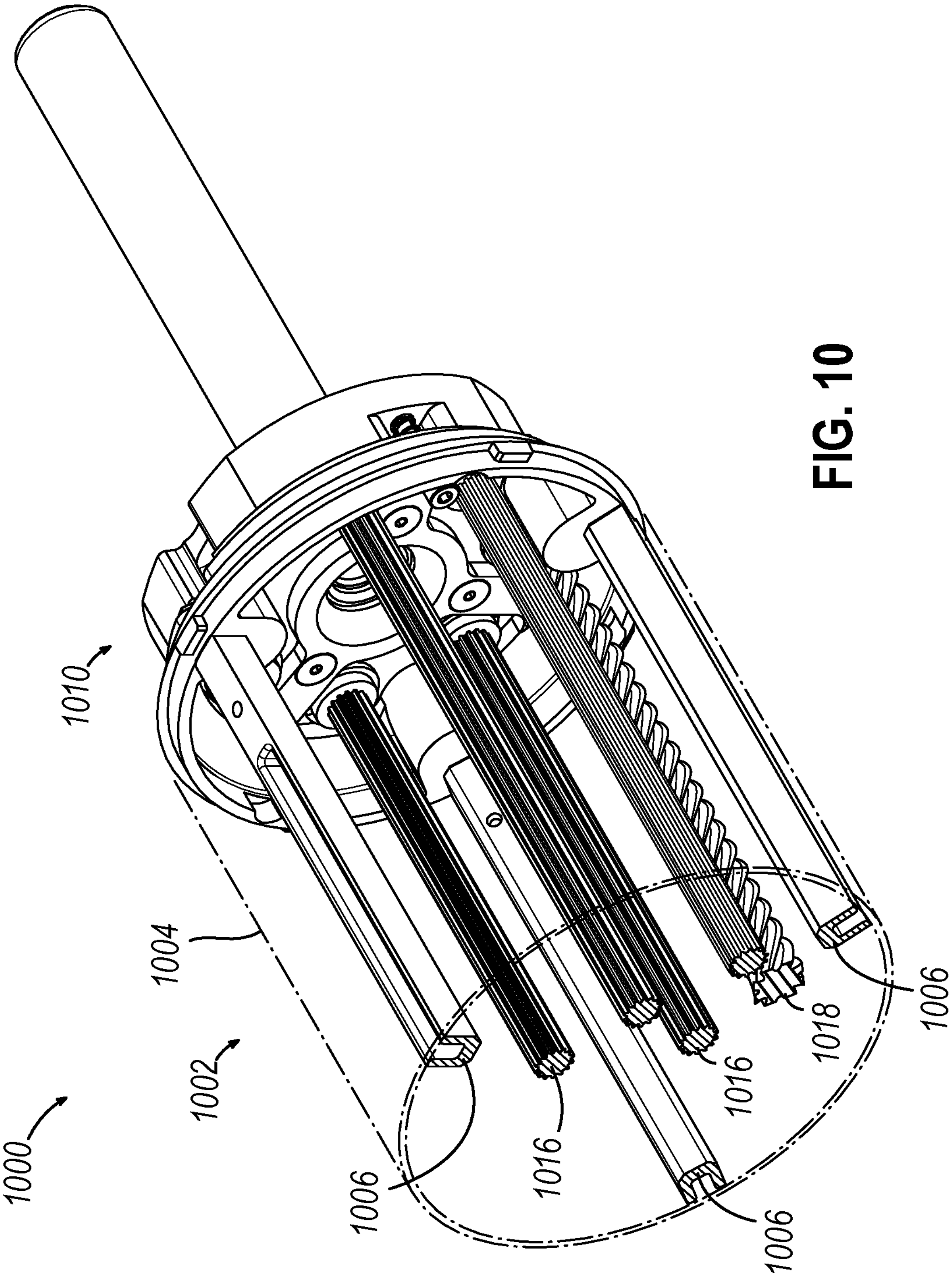
FIG. 10 depicts a sectional perspective view of the instrument base of FIG. 9 taken along section line 10-10 of FIG. 9, with selected portions being transparent for purposes of clarity.

FIGS. 9-10 show instrument base (1000). Instrument base (1000) includes a chassis housing (1002) and an attachment interface (1010). Chassis housing (1002) includes a cylindrical chamber (1004) dimensioned to slidably house a drive chassis (1034) (see FIG. 12) suitably attached to shaft assembly (114).

With respect to FIGS. 9-10, attachment interface (1010) is configured to couple instrument base (1000) with a suitable instrument driver, similar to instrument driver (66) described above. Attachment interface (1010) includes a plurality of drive inputs (1012), a plurality of elongated splined shafts (1016) extending proximally from respective drive inputs (1012) into the interior of cylindrical chamber (1004), and an elongated threaded rod (1018) extending proximally from a respective drive input (1012) into the interior of cylindrical chamber (1004).

Drive inputs (1012) may be independently rotated about their own axis. Similar to drive inputs (80) described above, drive inputs (1012) are configured to respectively couple with corresponding drive outputs of a suitable robotic arm (similar to drive outputs (68) of robotic arm (32) described above). Therefore, drive outputs of a suitable robotic arm are configured to independently rotate drive inputs (1012) about their own axis relative to interface plate (1014).

Drive inputs (1012) are operatively attached to a respective elongated splined shaft (1016) or elongated threaded rod (1018) such that rotation of drive inputs (1012) leads to rotation of the respective elongated splined shaft (1016) or threaded rod (1018). In some instances, a gear train (1014) (see FIG. 15) operatively couples drive input (1012) with a respective elongate splined shaft (1016) or threaded rod (1018).

Splined shafts (1016) and threaded rod (1018) extend proximally from drive inputs (1012) into a proximal end of chassis housing (1002) along a respective longitudinal axis, where each respective longitudinal axis is parallel with longitudinal axis (LA) shown in further reference to FIG. 11A. Splined shafts (1016) and threaded rod (1018) are each rotatably supported within chassis housing (1002). Splined shafts (1016) and threaded rod (1018) may be rotatably supported within chassis housing (1002) via any suitable features as would be apparent to one skilled in the art in view of the teachings herein. For example, splined shafts (1016) and threaded rod (1018) may be coupled to proximal end of chassis housing (1002) via rotatory bearings.

Therefore, splined shafts (1016) and threaded rods (1018) are independently rotatable about their own longitudinal axis via interaction between respective drive inputs (1012) and corresponding drive outputs (similar to drive outputs (68) described above). Splined shaft (1016) and threaded rods (1018) may be suitably coupled to respective portions of drive chassis (1034) such that rotation of respective splined shafts (1016) and threaded rod (1018) drives actuation of shaft assembly (114) and/or end effector (116) in accordance with the description herein.

While in the current example, there are six drive inputs (1012), any suitable number of drive inputs (1012) may be used as would be apparent to one skilled in the art in view of the teachings herein. Also, in the current example, there are four splined shafts (1016), but any other suitable number of splined shafts (1016) may be used as would be apparent to one skilled in the art in view of the teachings herein.

Figure 12:
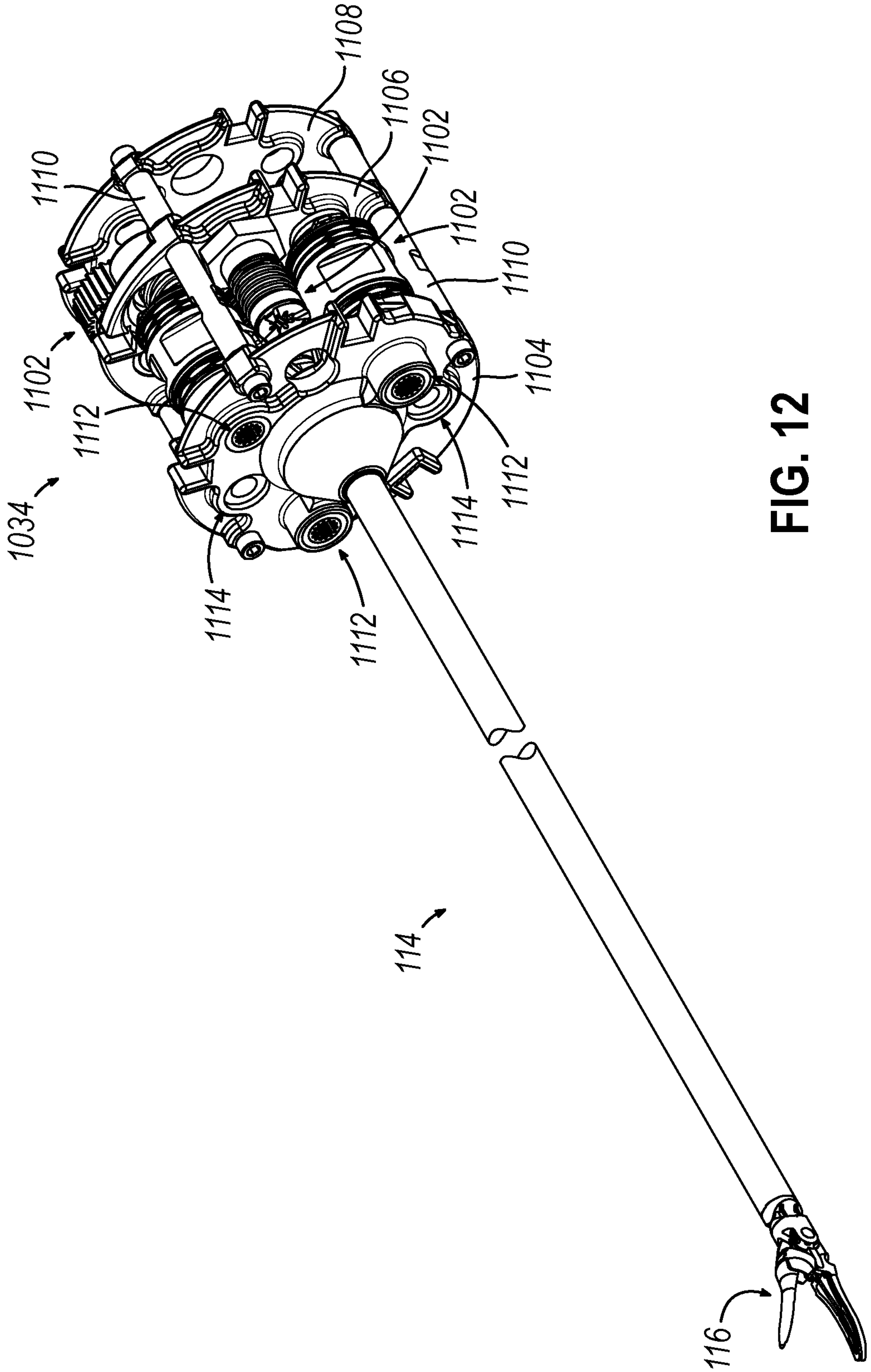
FIG. 12 depicts a perspective view of the shaft assembly and the end effector of FIG. 11A.

Turning to FIG. 12, shaft assembly (114) extends distally into end effector (116), which may be substantially similar to shaft assembly (114) and end effector (116) described above, with differences elaborated below. A proximal end of shaft assembly (1030) is attached to a drive chassis (1034). As mentioned above, drive chassis (1034) is slidably housed within cylindrical chamber (1004). In the current example, drive chassis (1034) includes a plurality of drive input assemblies (1102), a distal chassis plate (1104), an intermediate chassis plate (1106), and a proximal chassis plate (1108). Chassis plates (1104, 1106, 1108) are fixed to each other via coupling members (1110) and are rotationally restrained relative to chassis housing (1002). Further, chassis plates (1104, 1106, 1108) rotatably support the plurality of drive input assemblies (1102). Therefore, chassis plates (1104, 1106, 1108) act as a mechanical frame for drive input assemblies (1102).

Each chassis plate (1104, 1106, 1108) also defines a plurality of openings (1114). Openings (1114) of individual chassis plates (1104, 1106, 1108) are aligned with corresponding openings (1114) of other chassis plates (1104, 1106, 1108) along an axis that extends parallel with longitudinal axis (LA). Aligned openings (1114) are associated with a respective drive input assembly (1102) and dimensioned to receive either splined shaft (1016) (see FIG. 10) or threaded rod (1018) (see FIG. 10) such that the received splined shaft (1016) (see FIG. 10) or threaded rod (1018) (see FIG. 10) suitably interacts with the corresponding drive input assembly (1102) in accordance with the description herein.

In the current example, threaded rod (1018) (see FIG. 10) is configured to threadedly engage its respective drive input assembly (1102) such that rotation of threaded rod (1018) drives translation of drive chassis (1034) within chamber (1004) of chassis housing (1002) (see FIG. 10). Therefore, rotation of threaded rod (1018) in accordance with the description herein is configured to drive translation of shaft assembly (114) and end effector (116) relative to instrument base (1000) as shown between FIGS. 11A-11B.

Drive input assemblies (1102) configured to operatively couple with a respective spline (1016) (see FIG. 10) may comprise at least one internal splined rotary body (1112) rotatably supported by at least one chassis plate (1104, 1106, 1108) such that splined rotary bodies (1112) may rotate relative to chassis plates (1104, 1106, 1108). Internal spline rotary bodies (1112) are configured to drive rotation of their respective drive input assembly (1102) in order to actuate end effector (116) in substantially similar manner as to how drive inputs (80) actuate movement of end effector (116) described above. Therefore, internal spline rotary bodies (1112) may be operatively coupled to other components of a respective drive input assembly (1102) via any suitably components as would be apparent to one skilled in the art in view of the teachings herein. For example, a spur gear, a bevel gear, a worm gear, a helical gear, an oblique camming assembly, etc. may be attached to internal spline rotary body (1112) in order to convert rotational movement of spline rotary body (1112) into mechanical movement that may actuate end effector (116) in a substantially similar manner as end effector (116) described above.

Internal spline rotary bodies (1112) are configured to slide along the length of a respective spline (1016) in response to translation drive chassis (1034) in accordance with the description herein. Additionally, internal spline rotary bodies (1112) are configured to remain engaged with respective splines (1016) such that rotation of spline (1016) in accordance with the description herein also drives rotation of a respective internal spline rotary bodies (1112). In other words, internal spline rotary bodies (1112) are slidably coupled with a respective spline (1016), yet rotationally fixed to the respective spline (1016) about the longitudinal axis of spline (1016). Therefore, drive chassis (1034) is configured to translate within chassis housing (1002) while also maintaining operative engagement splines (1016), thereby allowing a robotic arm suitably attached to interface (1010) to suitably control end effector (116) in accordance with the description herein.

II. Illustrative Knife Drive Mechanism

As mentioned above, in instances where a cable is used to actuate knife member (125) within knife channel (124) between the proximal and distal positions, such a cable may be attached to a first drive input (80) dedicated to distally actuating knife member (125); while the cable may also be attached to a second drive input (80) dedicated to proximally actuating knife member (125). In such instances, the first drive input (80) and the second drive input (80) rotate synchronously such that one drive input (80) feeds the cable in response to movement of knife member (125), while the other drive input (80) simultaneously receives and further spools the cable in response to pulling knife member (125) in either the proximal or distal direction. A series of pulleys may be used to guide the cable along a predetermined path, while knife member (125) is attached to a location on cable such that cable drives knife member (125) in accordance with the description herein.

However, in some instances, the number of drive inputs (80, 1012) may be limited, such that two drive inputs (80, 1012) may not be readily available to synchronically feed and receive the cable utilized to fire knife member (125). Therefore, in some instances, it may be desirable to utilize a single drive input (80, 1012) that is configured to synchronously feed and receive opposite ends of a cable to thereby fire knife member (125) in accordance with the description herein.

Figure 13:
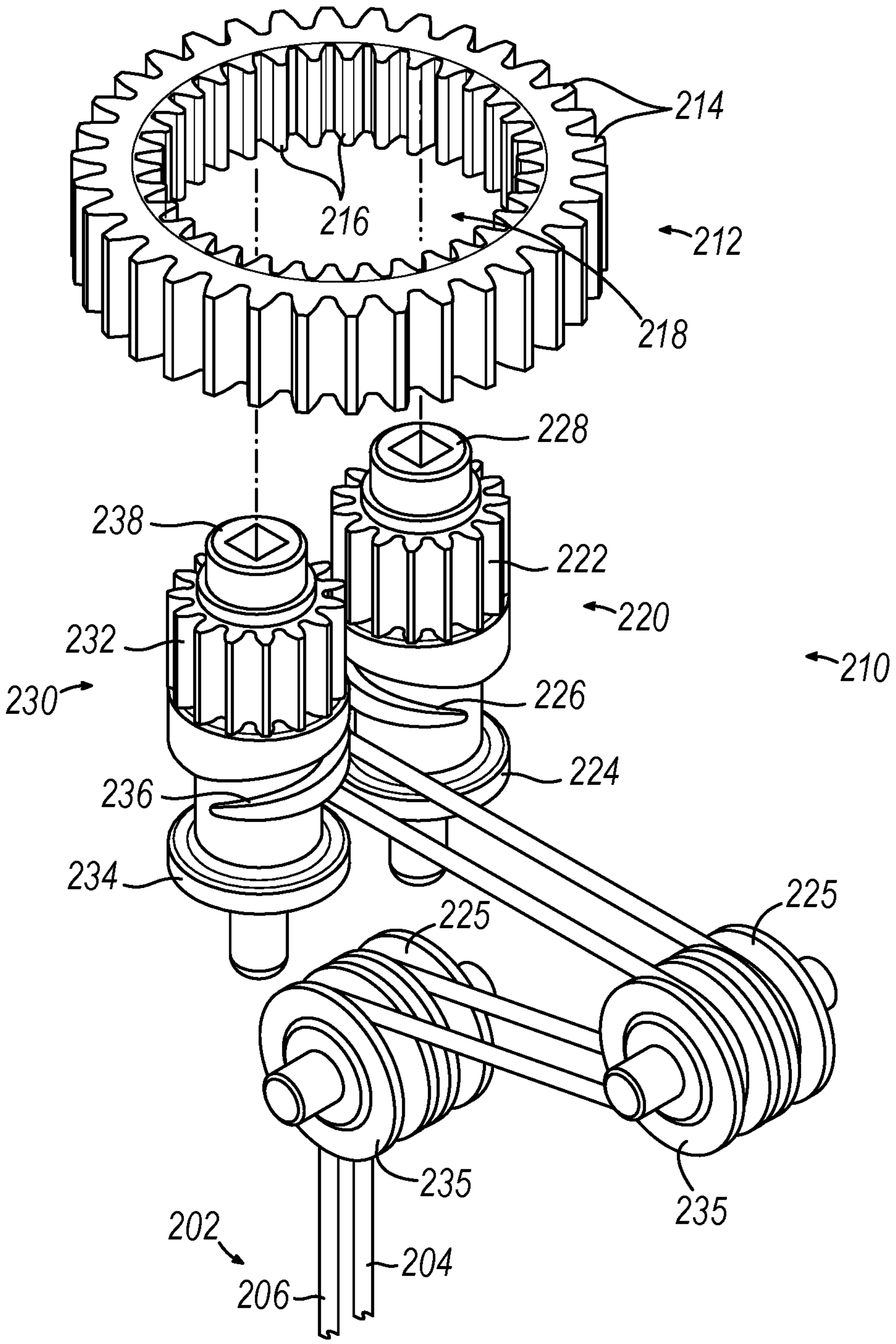
FIG. 13 depicts a perspective exploded view of an illustrative drive input assembly of a knife driving assembly; that may be used to drive the knife member of FIG. 7C.
Figure 14:
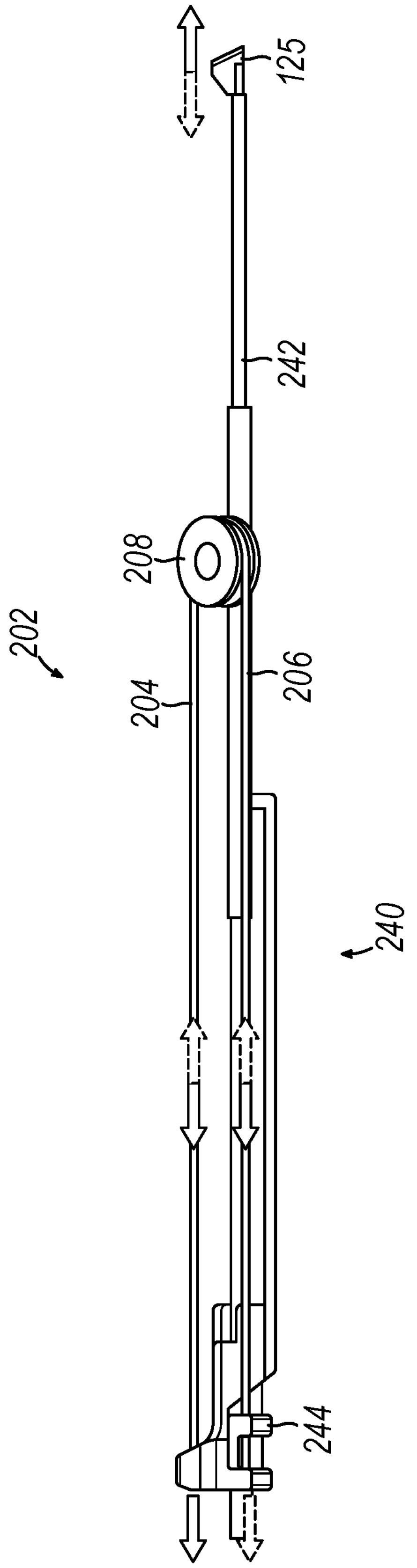
FIG. 14 depicts a side elevational view of an illustrative distal portion of the knife driving assembly of FIG. 13.
Figure 15:
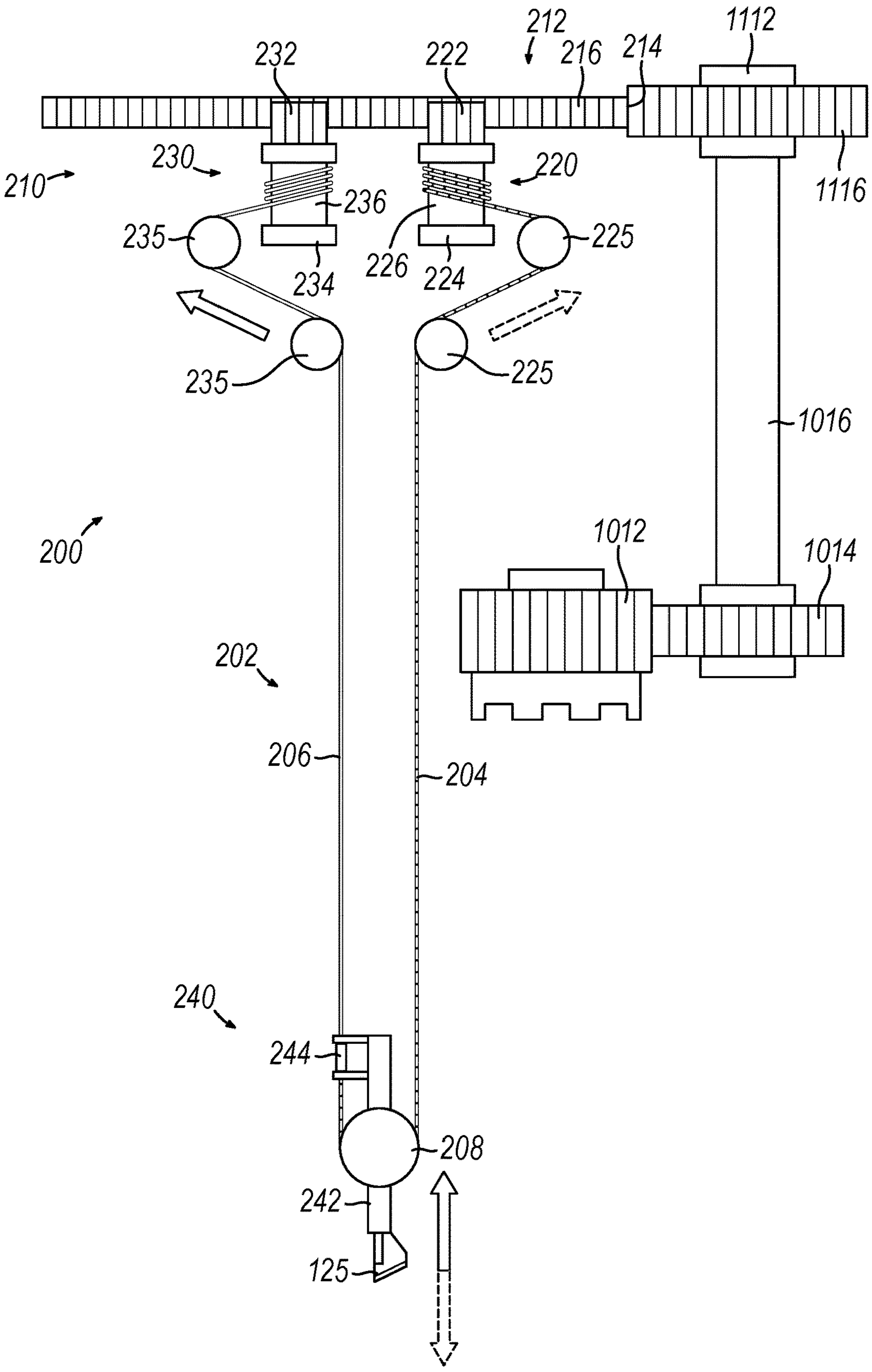
FIG. 15 depicts a top plan view of the knife driving assembly of FIG. 13 coupled to a drive input, a gear train, a spline shaft, an internal splined rotary body, and a gear of the instrument base of FIG. 9.

FIG. 13 shows a drive input assembly (210) of an illustrative knife driving assembly (200); while FIG. 14 shows a distal portion (240) of knife driving assembly (200); and FIG. 15 shows drive input assembly (210) and distal portion (240) of knife driving assembly (200) suitability attached to an elongated splined shaft (1016) of instrument base (1000) described above. As will be described in greater detail below, drive input assembly (210) is configured to operatively couple to a single drive input (1012) of attachment interface (1010) such that rotation of a single drive input (1012) in a first rotational direction and a second rotational direction may drive a knife firing cable (202) to respectively distally advance knife member (125) and proximally retract knife member (125).

Knife drive input assembly (210) may be readily incorporated into drive chassis (1034) described above in replacement of one of the drive input assemblies (1102) rotatably attached to one or more chassis plates (1104, 1106, 1108). While in the current example, drive input assembly (210) is operably attached to suitable portions of drive chassis (1034) and instrument base (1000), it should be understood that drive input assembly (210) may be modified to be operatively attached to a drive input (80) described above.

Turning back to FIG. 13, drive input assembly (210) includes a ring gear (212) having both external teeth (214) and internal teeth (216), a first cable feed assembly (220), and a second cable feed assembly (230). First cable feed assembly (220) includes a first internal gear (222), a first capstan (224) having a cable feed body (226), and a rotational coupling section (228) configured to rotationally couple assembly (220) to suitable components. Similarly, second cable feed assembly (230) includes a second internal gear (232), a second capstan (234) having a cable feed body (236), and a rotational coupling section (238) configured to rotationally couple assembly (230) to suitable components.

As best shown in FIG. 15, external teeth (214) of ring gear (212) are configured to suitably engage a complementary gear (1116) attached to internally splined rotary body (1112). Complementary gear (1116) is attached to internally splined rotary body (1112) such that gear (1116) and body (1112) unitarily rotate and translate together. Therefore, rotation of drive input (1012) in accordance with the description herein is configured to drive rotation of gear train (1014), splined shaft (1016), internally splined rotary body (1112), complementary gear (1116), and ring gear (212).

Additionally, ring gear (212), capstans (220, 230), and pulleys (225, 235) may be rotatably supported by suitable portions of drive chassis (1034), such as one or more chassis plates (1104, 1106, 1108). Therefore, as internally splined rotary body (1112) and complementary gear (1116) translate along the length of spline (1016) to thereby advance and retract shaft assembly (114) and end effector (116) in accordance with the description herein; knife driving assembly (200) also advances and retracts along with shaft assembly (114) and end effector (116) such that ring gear (212) remains operatively engaged with complementary gear (1116).

Internal gears (222, 232) of cable feed assembly (220, 230) are housed within an opening (218) of ring gear (212) and suitably mesh with internal teeth (216) of ring gear (212). Therefore, rotation of ring gear (212) caused by rotation of complementary gear (1116) also drives rotation of cable feed assemblies (220, 230). Cable feed assemblies (220, 230) are configured to be simultaneously rotated by ring gear (212) in the same angular direction.

Cable (202) includes a first portion (204) associated with first cable feed assembly (220) and a second portion (206) associated with second cable feed assembly (230). An end of first portion (204) of cable (202) is spooled around cable feed body (226) of first capstan (224) such that rotation of first capstan (224) in a first rotational direction receives/spools first portion (204) of cable (202), and rotation of capstan (224) in a second rotational direction feeds first portion (204) of cable (202) away from cable feed body (226). Conversely, an end of second portion (206) of cable (202) is spooled around cable feed body (236) of second capstan (234) such that rotation of second capstan (234) in the first rotational direction feeds the second portion (206) of cable (202) away from cable feed body (236), and rotation of capstan (234) in the second rotational direction receives/spools the second portion (206) of cable (202).

Therefore, if first capstan (224) and second capstan (226) rotate in the same angular direction, one capstan (224, 234) will feed cable (202) away from itself and the opposite capstan (224, 234) will simultaneously receive/spool cable (202). Since ring gear (212) is configured to simultaneously drive rotation of cable feed assemblies (220, 230) in the same angular direction, rotation of ring gear (212) is configured to simultaneously actuate one capstan (224, 234) to feed cable (202) and the other capstan (224, 234) to spool cable (202).

Portions (204, 206) of cable (202) extending away from respective feed assemblies (220, 230) are suitably engaged with respective pulleys (225, 235) in order to guide portions (204, 206) of cable (202) to loop around distal pulley (208) of distal portion (240).

Distal portion (240) of knife driving assembly (240) includes a translating body (242), a cable coupling carriage (244), and distal pulley (208). Cable (202) loops around distal pulley (208) such that distal pulley (208) guides cable (202) back toward cable feed assemblies (220, 230). If first portion (204) of cable (202) is being retracted proximally, guide pulley (208) directs cable (202) such that second portion (206) of cable (202) is advanced distally, and vice versa.

Therefore, ring gear (212) may rotate cable feed assemblies (220, 230) in a first rotational direction such that first capstan (224) spools cable (202) while second capstan (234) feeds cable (202) in order to distally advance second portion (206) of cable (202). Conversely, ring gear (212) may rotate cable feed assemblies (220, 230) in a second, opposite, rotational direction such that second capstan (234) spools cable (202) while first capstan (224) feeds cable (202) in order to proximally retract second portion (206) of cable (202).

Translating body (242) is attached to knife member (125) such that movement of translating body (242) is configured to drive corresponding movement of knife member (125). Carriage (244) is fixed to both translating body (242) and second portion (206) of cable (202). Therefore, as second portion (206) of cable (202) is actuated along the path defined by cable feed assemblies (220, 230) and distal pulley (208) in accordance with the description herein, carriage (244) and translating body (242) follow second portion (206) of cable (202) in order to actuate knife member (125). Carriage (244) is attached to a corresponding portion of cable (202) such that as cable (202) travels along the path defined by cable feed assemblies (220, 230) and distal pulley (208), knife member (125) actuates within jaws (120, 122) between the proximal position (see FIGS. 17A and 17C) and the distal position (see FIG. 17B).

It should be understood distal portion (240) may be suitably housed within components of shaft assembly (114) and end effector (116) such that knife member (125) may suitably travel within jaws (120, 122) in accordance with the description herein.

Figure 16A:
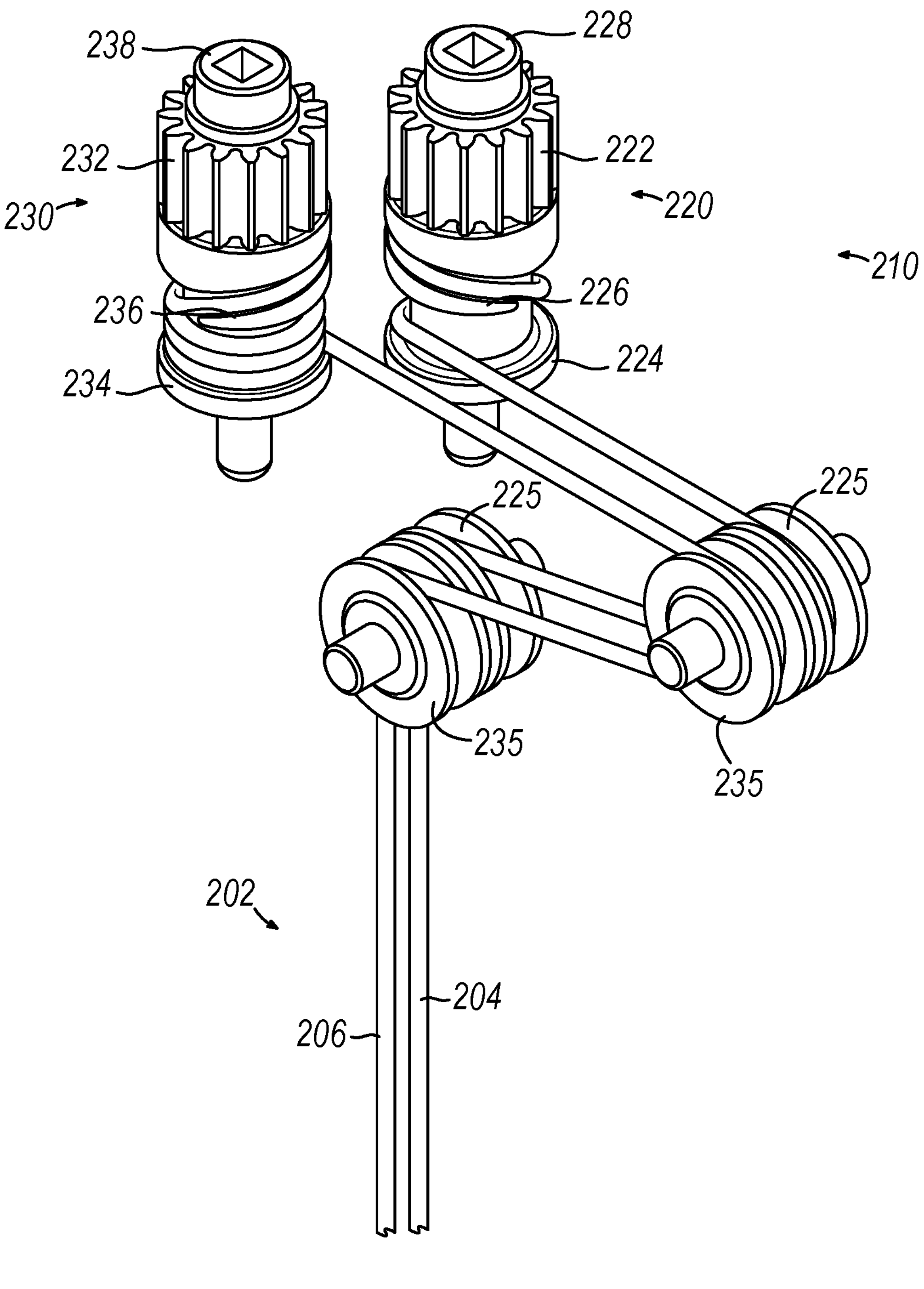
FIG. 16A depicts a perspective view of the drive input assembly of FIG. 13, with selected portions omitted for purposes of clarity, with the drive input assembly in a pre-fired position.
Figure 16B:
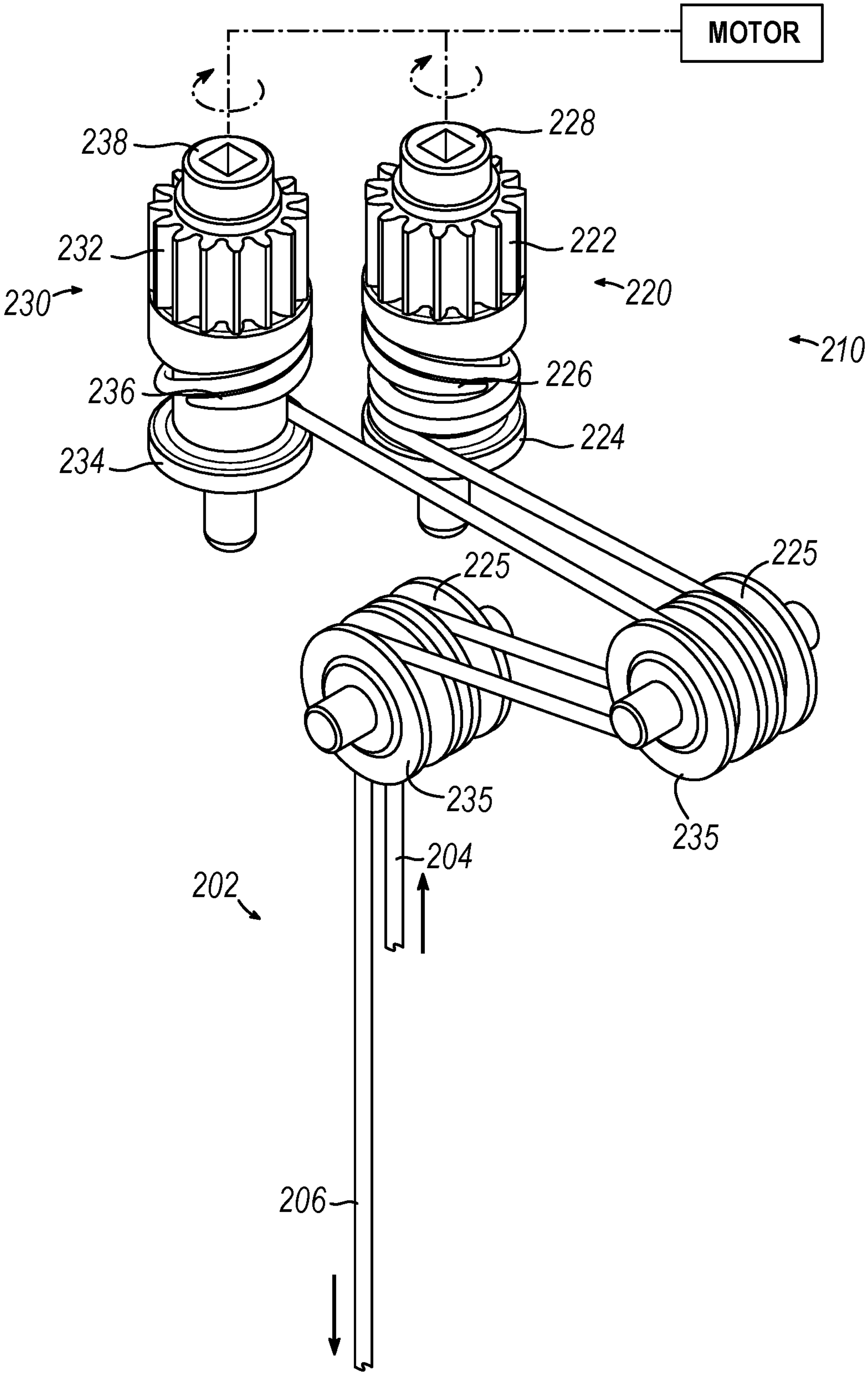
FIG. 16B depicts a perspective view of the drive input assembly of FIG. 13, coupled to a motorized output assembly and with selected portions omitted for purposes of clarity, with the drive input assembly rotated into a fired position.
Figure 16C:
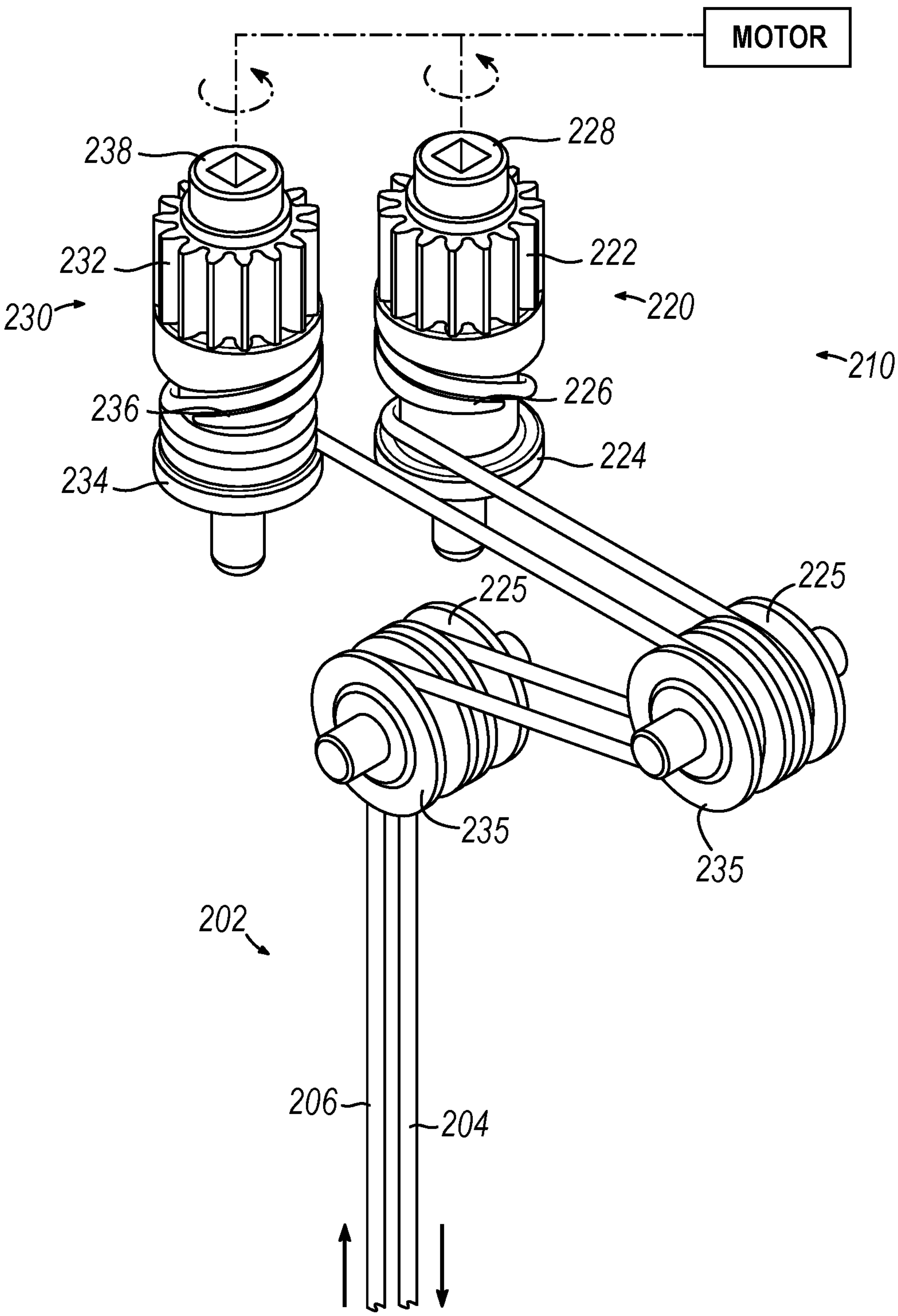
FIG. 16C depicts a perspective view of the drive input assembly of FIG. 13, coupled to a motorized output assembly and with selected portions omitted for purposes of clarity, with the drive input assembly rotated back into the pre-fired position.
Figure 17A:
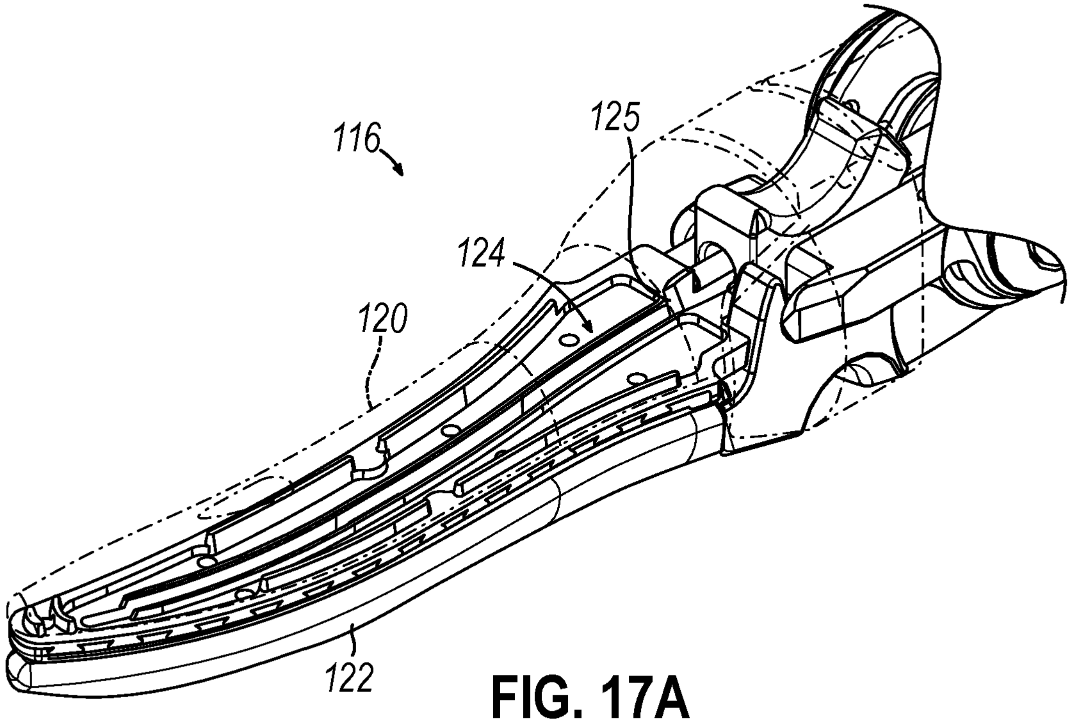
FIG. 17A depicts a perspective view of the end effector of FIG. 7A, with the jaws of FIG. 7A in a closed position and the knife member of FIG. 7C in a retracted position, with one jaw shown in phantom.
Figure 17B:
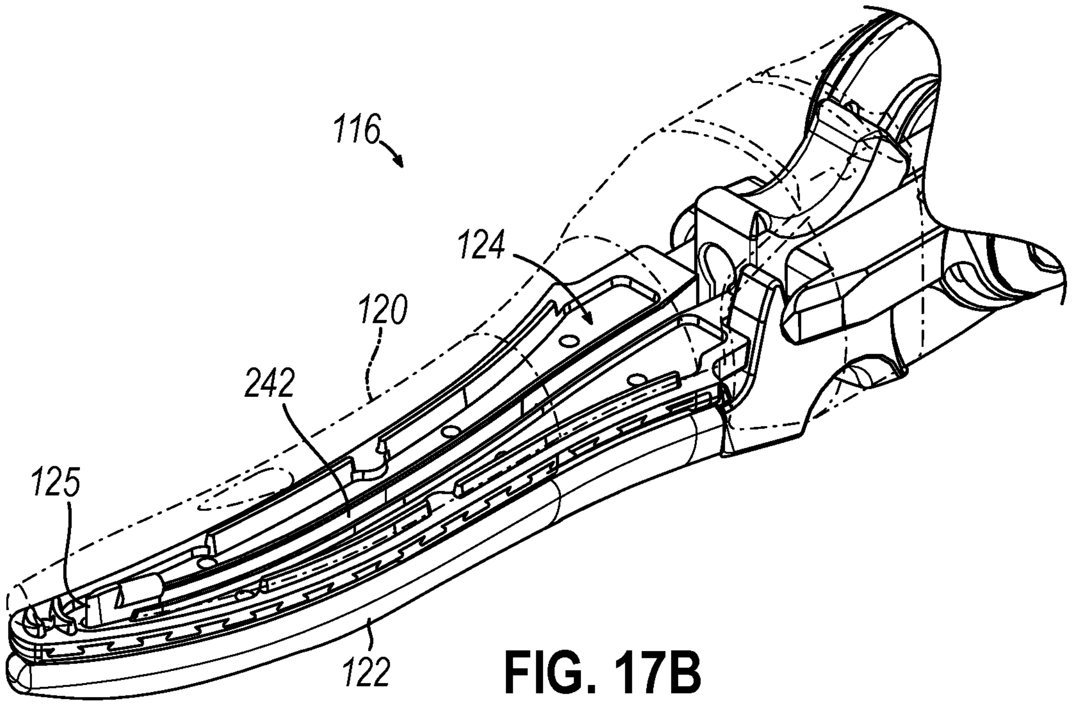
FIG. 17B depicts a perspective view of the end effector of FIG. 7A, with the jaws of FIG. 7A in a closed position and the knife member of FIG. 7C in the extended position, with one jaw shown in phantom.
Figure 17C:
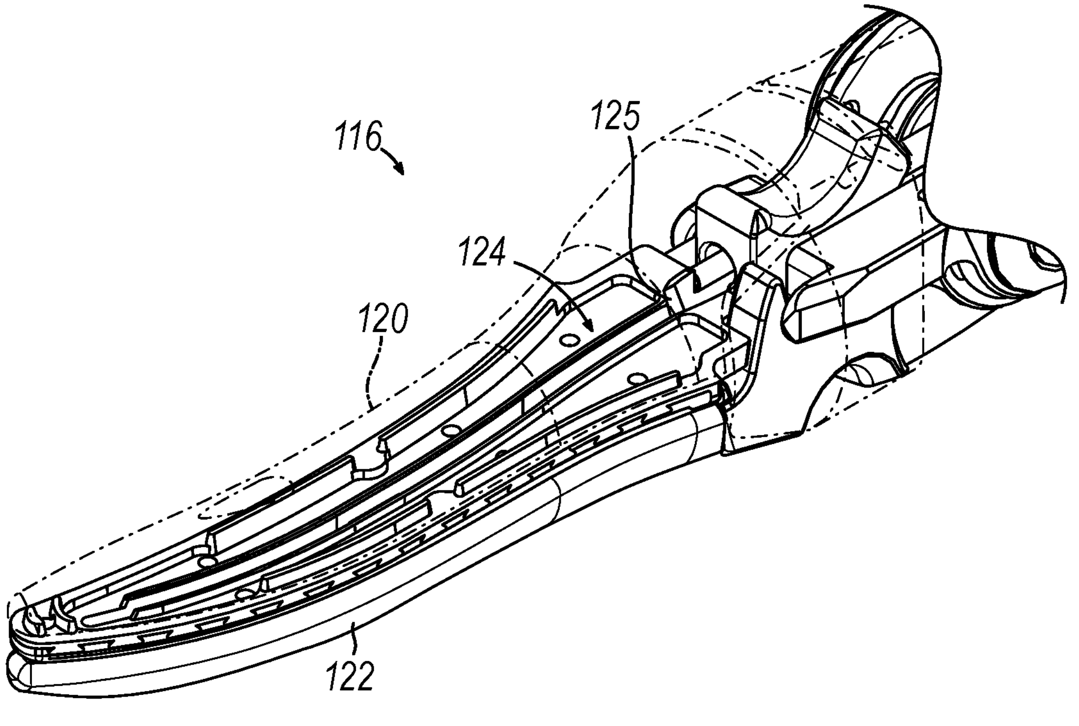
FIG. 17C depicts a perspective view of the end effector of FIG. 7A, with the jaws of FIG. 7A in a closed position and the knife member of FIG. 7C in the retracted position, with one jaw shown in phantom.

FIGS. 16A-16C show exemplary use of drive input assembly (210) in order to fire knife member (125) in accordance with the description herein; while FIG. 17A-17C show a corresponding firing of knife member (125) within end effector (116). For purposes of clarity, FIGS. 16A-16C omit ring gear (212). However, it should be readily understood that internal teeth (216) of ring gear (212) are operatively engaged with internal gears (222, 232).

FIGS. 16A and 17A show drive input assembly (210) and knife member (125), respectively, in a pre-fired position. When an operator desires to fire knife member (125) in accordance with the description herein, the operator may initiate a firing process that rotates both cable feed assemblies (220, 230) in a first angle direction, as shown in FIG. 16B. As mentioned above, rotation of cable feed assemblies (220, 230) in the first angular direction causes first portion (204) of cable (202) to be spooled by first cable feed assembly (220); while second portion (206) of cable (202) is fed out of second cable feed assembly (230). Therefore, at distal portion (240) of knife driving assembly (200), second portion (206) is advanced distally, while first portion (204) is retracted proximally.

Since carriage (244) is fixed to a second portion (206) (see FIGS. 14-15); carriage (244), translating body (242) and knife member (125) are each advanced distally in response to rotation of both cable feed assemblies (220, 230) in the first angular direction. As best shown in FIG. 17B, cable feed assemblies (220, 230) are rotated in the first angular direction until knife member (125) is advanced to a distal position within jaws (120, 122). Knife member (125) is advanced within knife channel (124), thereby severing tissue captured between jaws (120, 122).

Once knife member (125) is advanced to the distal end of jaws (120, 122), cable feed assemblies (220, 230) are then rotated in the second, opposite, angular direction. As mentioned above, rotation of cable feed assemblies (220, 230) in the second angular direction causes second portion (206) of cable (202) to be spooled by second cable feed assembly (230); while first portion (204) of cable (202) is fed out of first cable feed assembly (220). Therefore, at distal portion (240) of knife driving assembly (200), second portion (206) is retracted proximally, while first portion (204) is advanced distally.

Since carriage (244) is fixed to a second portion (206) (see FIGS. 14-15); carriage (244), translating body (242) and knife member (125) are each retracted proximally in response to rotation of both cable feed assemblies (220, 230) in the second angular direction. As best shown in FIG. 17C, cable feed assemblies (220, 230) are rotated in the first angular direction until knife member (125) is retracted back to the proximal position within jaws (120, 122).

Cable feed assembly (220, 230) are shown being rotate by a motor assembly in FIGS. 16B-16C. It should be readily understood that such a motor assembly may include drive input (1012), gear train (1014), splined shaft (1016), internally splined rotary body (1112), complementary gear (1116), and ring gear (212) as shown in FIG. 15. Additionally, it should be understood that drive input (1012) may be suitably attached to a rotary drive output (68) configured to drive rotation of drive input (1012) in accordance with the description herein.

It should be understood that knife driving assembly (200) may be operatively attached to a single drive input (1012) in order to both distally advance and proximally retract knife member (125) attached to a cable (202); rather than traditionally using two separate drive inputs (1012) in order to drive opposite ends of cable (202). Therefore, knife driving assembly (200) allows for suitable control of knife member (125) attached to cable (202) while only utilizing a single drive input (1012).

Figure 18A:
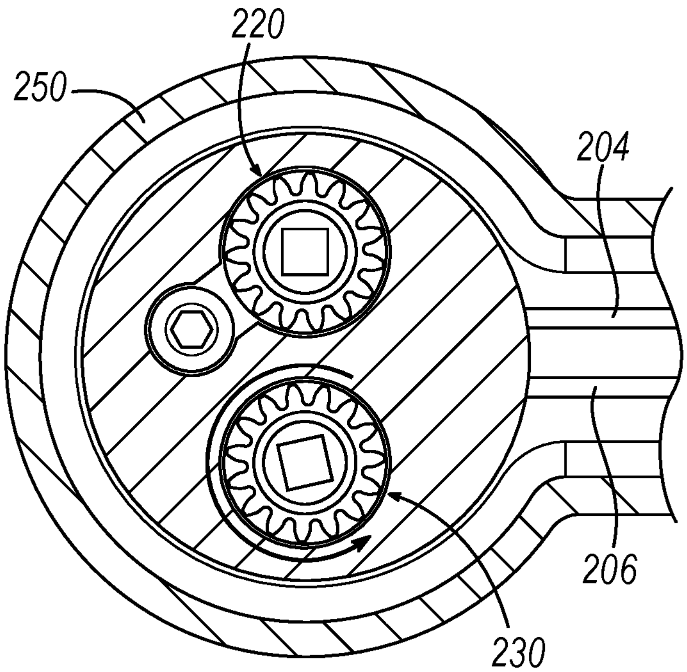
FIG. 18A depicts a top cross-sectional view of the drive input assembly of FIG. 13, with a ring gear removed in order to tension a firing cable to a first and second capstan.
Figure 18B:
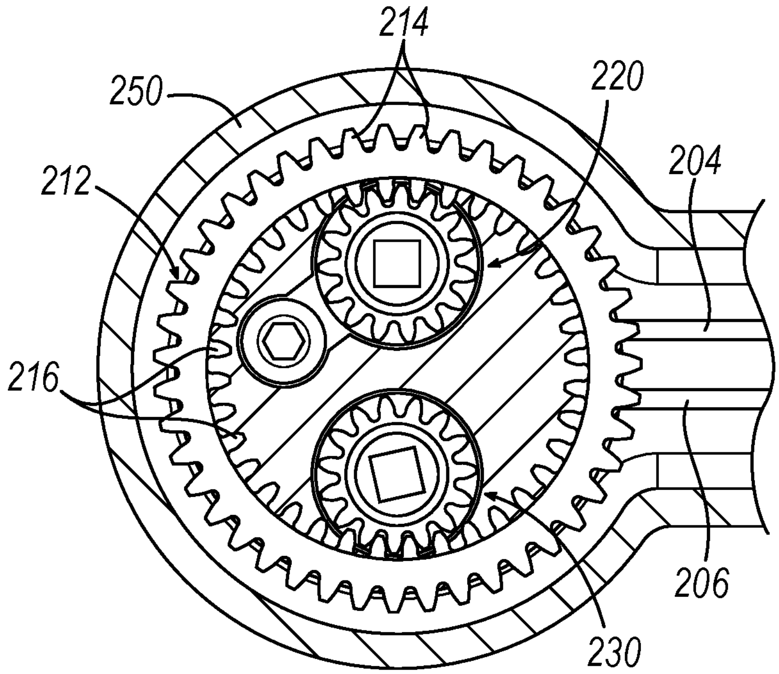
FIG. 18B depicts a top cross-sectional view of the drive input assembly of FIG. 13, with the ring gear installed.

FIGS. 18A-18B show an illustrative installation of drive input assembly (210) in order to provide suitable tension within cable (202) for suitably driving knife member (125) in accordance with the description herein. First, prior to installing ring gear (212) within a gear housing (250), an operator may suitably fix first cable feed assembly (220) such that cable feed assembly (220) is inhibited from rotating in either angular direction described above. At this moment in FIG. 18A, cable (202) is coupled to both cable feed assemblies (220, 230) and wrapped around distal pulley (208). With first cable feed assembly (220) substantially fixed, the operator may rotate second cable feed assembly (230) until a desirable amount of tension is present within cable (202).

Once a desirable amount of tension is present within cable (202), the operator may attach ring gear (212) are shown in FIG. 18B. The operator may then release first cable feed assembly (220) such that cable feed assembly (220) may rotate in accordance with the description herein.

III. Alternative Illustrative Knife Drive Mechanisms

Figure 19:
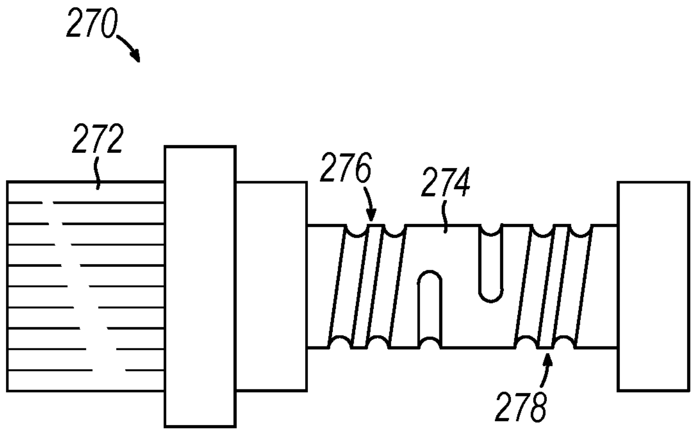
FIG. 19 depicts an elevational side view of a dual t threaded cable feed assembly.

While ring gear (212) and two cable feed assemblies (220, 230) are used in drive input assembly (210) to convert rotational motion of a single drive input (1012) into both distal and proximal actuation of knife member (125) coupled to a cable (202), any other suitable structures may be used as would be apparent to one skilled in the art in view of the teachings herein. FIGS. 19-20C show an alternative knife driving assembly (260) that may be incorporated to replace knife driving assembly (200) described above. Therefore, knife driving assembly (260) may be substantially similar to knife driving assembly (200) described above, with differences elaborated below. Driving assembly (260) includes a drive input assembly (262) operatively coupled to distal portion (240) via cable (202).

Rather than portions (204, 206) of cable (202) being connected to separate cable feed assemblies (220, 230) that are each optatively engaged with ring gear (212); portions (204, 206) of cable (202) are attached to a single cable feed assembly (270). As shown in FIG. 19, dual threaded cable feed assembly (270) includes a gear (272), and a capstan (274) having a first cable feed section (276) and a second, opposite, cable feed section (278).

Gear (272) is operatively engaged with a complementary gear (262) that is driven by gear (1116). In other words, complementary gear (262) is interposed between gears (1116, 262) such that a single drive input (1012) may rotate gear (272) in a first angular direction and a second, opposite, angular direction in accordance with the description herein. Complementary gear (262) may have any suitable structure as would be apparent to one skilled in the art in view of the teachings herein. In some instances, gear (272) is directly coupled to gear (1116) such that complementary gear (262) is not present. Cable feed assembly (270) and gear (262) may be rotatably supported by any suitable structures in similar fashion to how cable feed assemblies (220, 230) and ring gear (212) are rotatable supported in accordance with the description above. Therefore, it should be understood that knife driving assembly (260) may translate with internally splined rotary body (1112) relative to elongated spline (1016) in accordance with the description herein.

First cable feed section (276) is configured to receive portion (206) of cable (202), while second, opposite, cable feed section (278) is configured to receive portion (204) of cable (202). In particular, in response to rotation of cable feed assembly (270) in a single angular direction, cable feed sections (276, 278) are configured to simultaneously feed a first portion (204, 206) of cable (202) away from cable feed assembly (270) while spooling/receiving the opposite portion (204, 206) of cable (202). Therefore, cable feed assembly (270) may be rotated in a first angular direction to drive knife member (125) distally, and then rotated in a second, opposite, angular direction to retracted knife member (125) proximally.

Figure 20A:
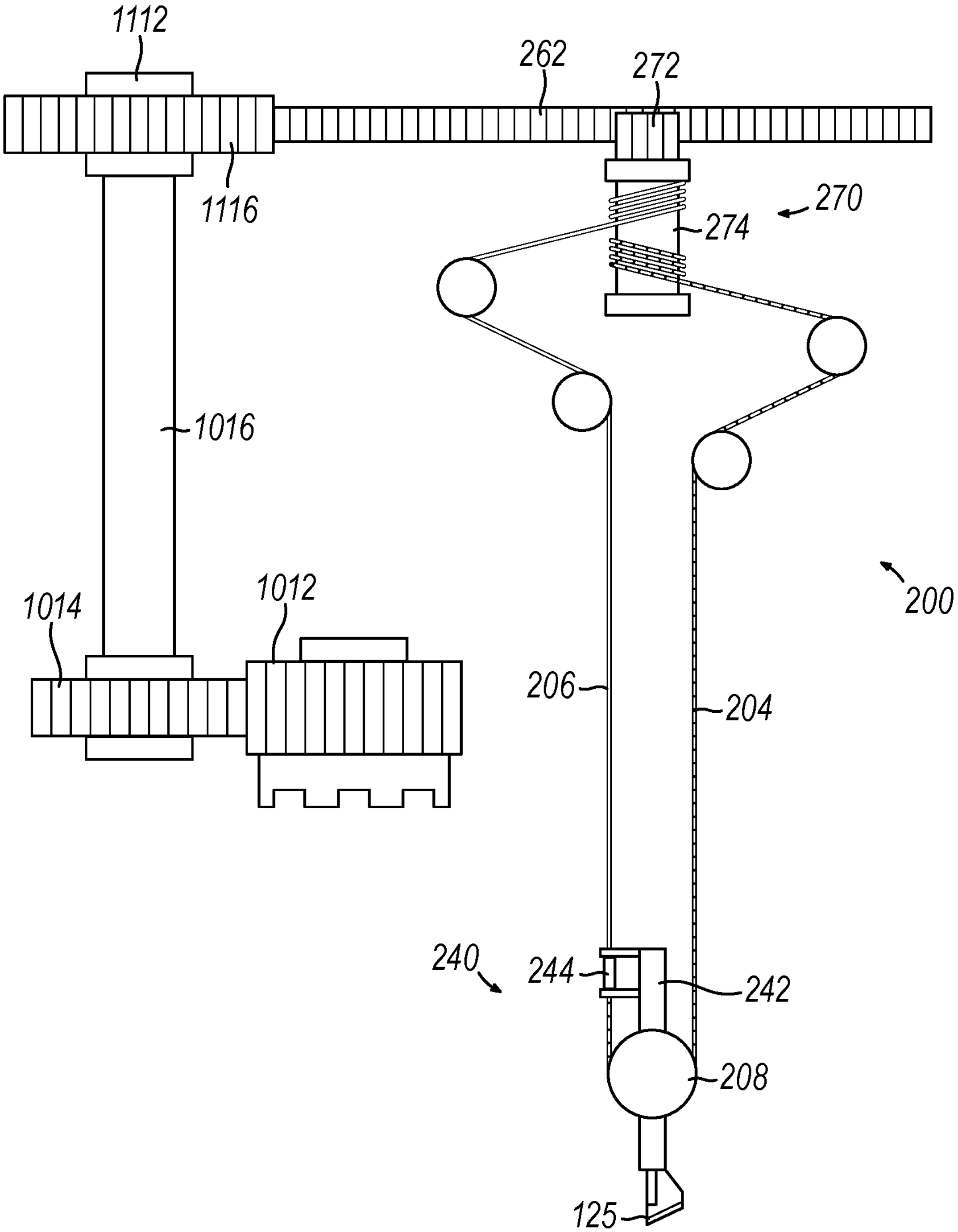
FIG. 20A depicts a top plan view of an alternative knife driving assembly in a pre-fired position.
Figure 20B:
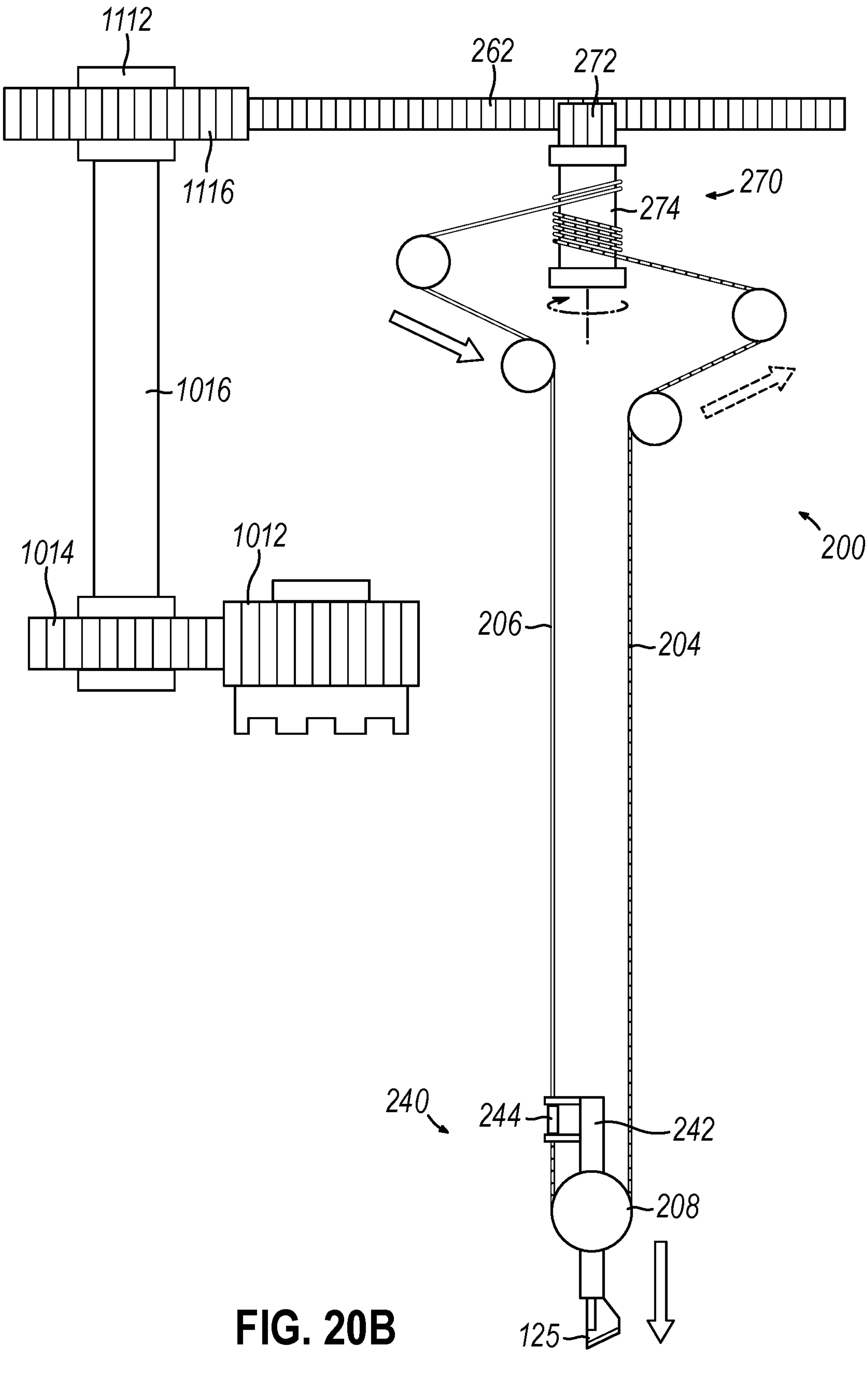
FIG. 20B depicts a top plan view of the knife driving assembly of FIG. 20A in a fired position.
Figure 20C:
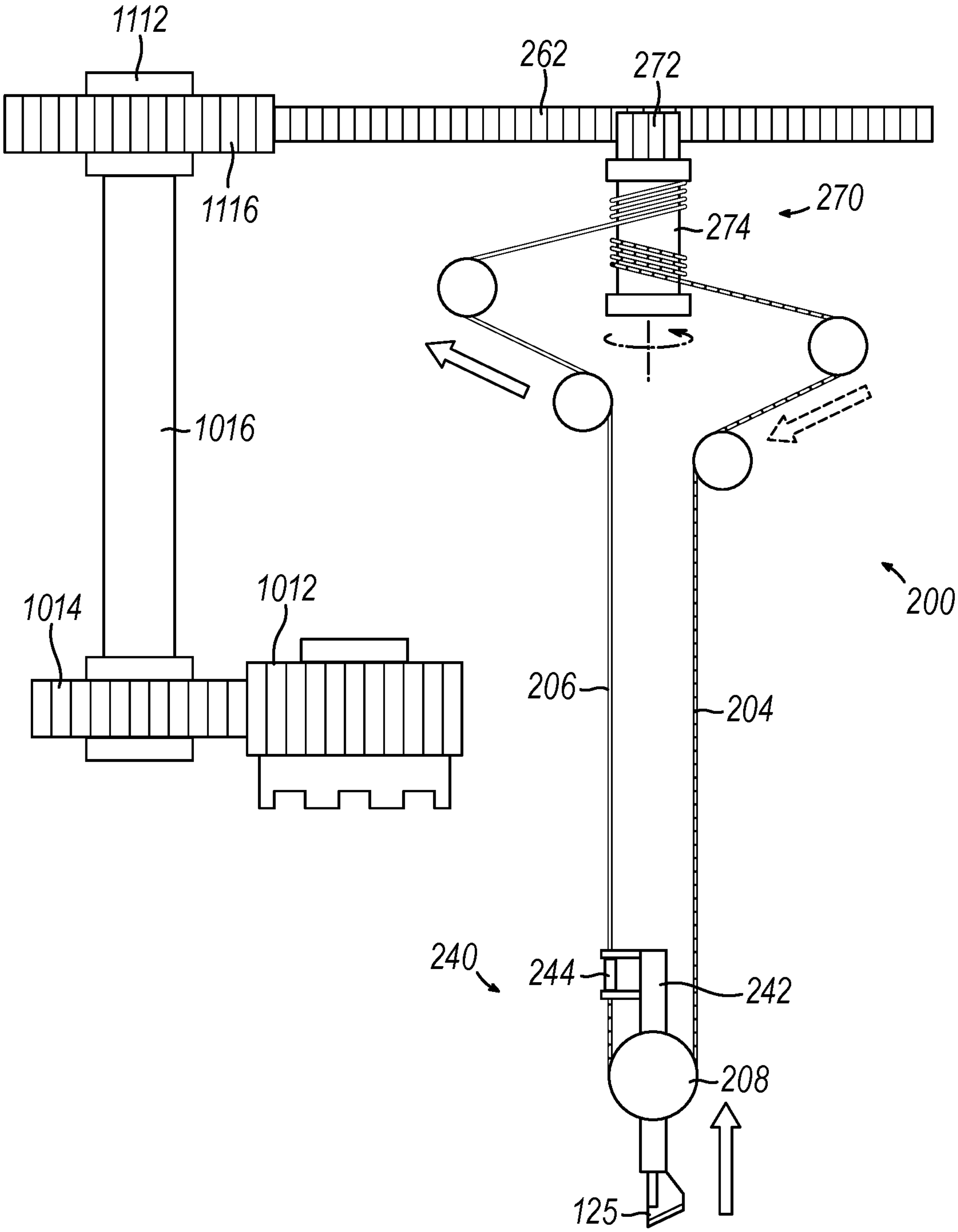
FIG. 20C depicts a top plan view of the knife driving assembly of FIG. 20A retracted from the fired position.

FIGS. 20A-20C show an exemplary firing of knife member (125) utilizing knife driving assembly (260). First, as shown in FIGS. 20A-20B, dual threaded cable feed assembly (270) may be rotated in a first angular direction. Rotation in the first angular direction spools portion (204) of cable (202) toward cable feed assembly (270) and simultaneously feeds portion (206) of cable (202) away from cable feed assembly (270). Distal movement of portion (206) of cable (202) drives knife member (125) distally in accordance with the description herein.

Once knife member (125) reaches the fired position, dual threaded cable feed assembly (270) may be rotated in the second, opposite, angular direction. Rotation in the second, opposite, angular direction spools portion (206) of cable (202) toward cable feed assembly (270) and simultaneously feeds portion (204) of cable (202) away from cable feed assembly (270). Proximal movement of portion (206) of cable (202) drives knife member (125) proximally in accordance with the description herein.

Figure 21:
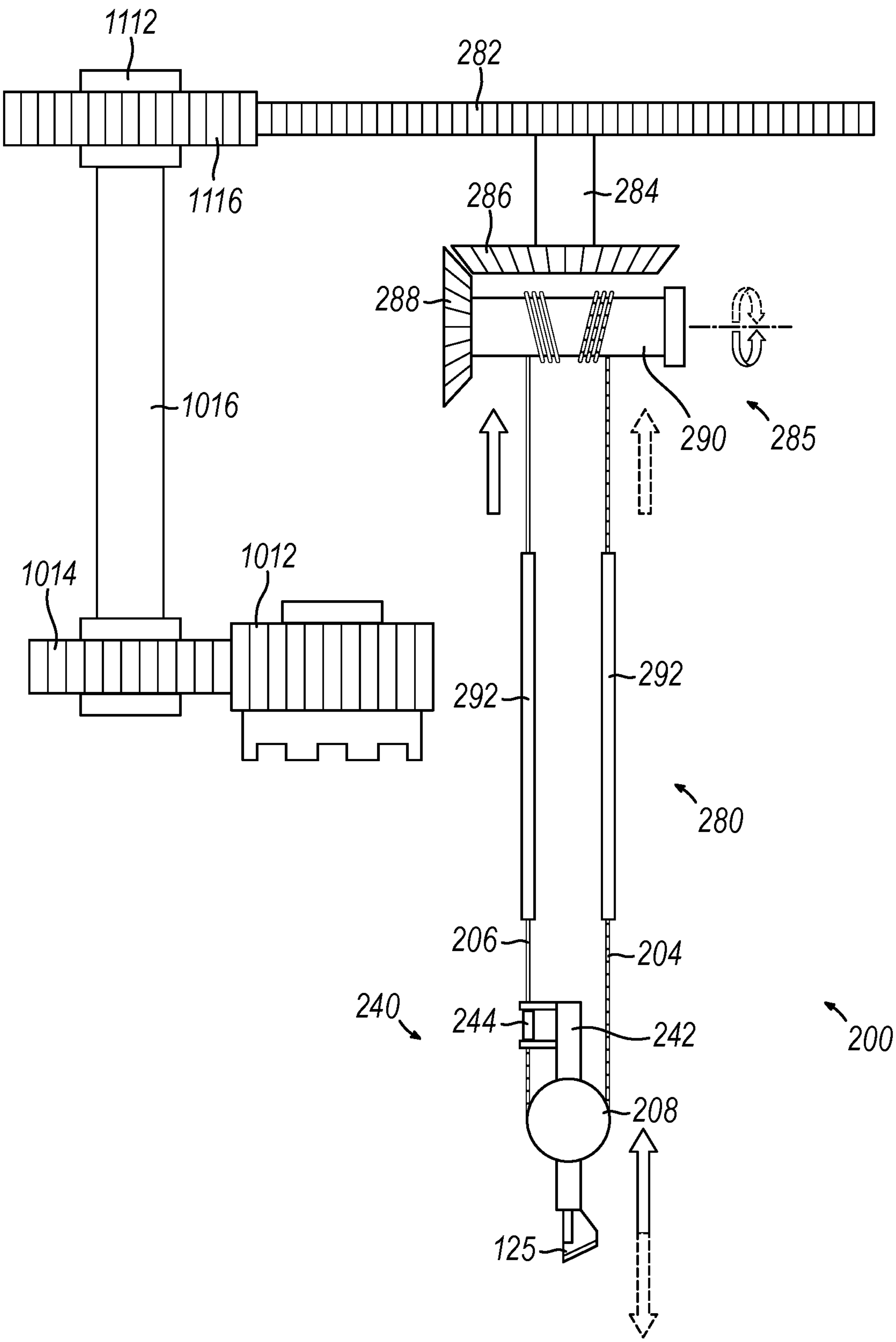
FIG. 21 depicts a top plan view of an alternative knife driving assembly.

FIG. 21 shows an alternative knife driving assembly (280) that may be incorporated to replace knife driving assembly (200, 260) described above. Therefore, knife driving assembly (280) may be substantially similar to knife driving assembly (200, 260) described above, with differences elaborated below. Driving assembly (280) includes a drive input assembly (285) operatively coupled to distal portion (240) via cable (202). Guide members (292) are utilized in the current example to help support portions (204, 206) of cable (202) as would be apparent to one skilled in the art in view of the teachings herein.

Portions (204, 206) of cable (202) are operatively coupled to a dual threaded cable feed assembly (290) that is configured to simultaneously feed a first portion (204, 206) of cable (202) away from cable feed assembly (290) while spooling/receiving the opposite portion (204, 206) of cable (202) in response to rotation in a single angular direction. Therefore, rotation of cable feed assembly (290) in a first angular direction distally advance knife member (125), while rotation of cable feed assembly (290) in a second, opposite, angular direction proximally retracted knife member (125).

However, dual threaded cable feed assembly (290) in the current example is rotated via a plurality of gears (282, 286, 288) that are driven by gear (1116) such that a single drive input (1012) may rotate gears (282, 286, 288) in a first angular direction and a second, opposite, angular direction in accordance with the description herein. Gear (282) is directly coupled to first bevel gear (286) via a shaft (284), while first bevel first (286) meshes with second bevel gear (288) in order to suitably rotate second bevel gear (288). Second bevel gear (288) is fixed to cable feed assembly (290) such that rotation of second bevel gear (288) drives rotation of cable feed assembly (290). Therefore, gears (282, 286, 288) may be rotated in a first angular direction and a second angular direction in order to drive knife member (125) distally and proximally in accordance with the description herein. Gears (282, 286, 288) and cable feed assembly (290) may be rotationally supported by suitable features as would be apparent to one skilled in the art in view of the teachings herein.

Figure 22:
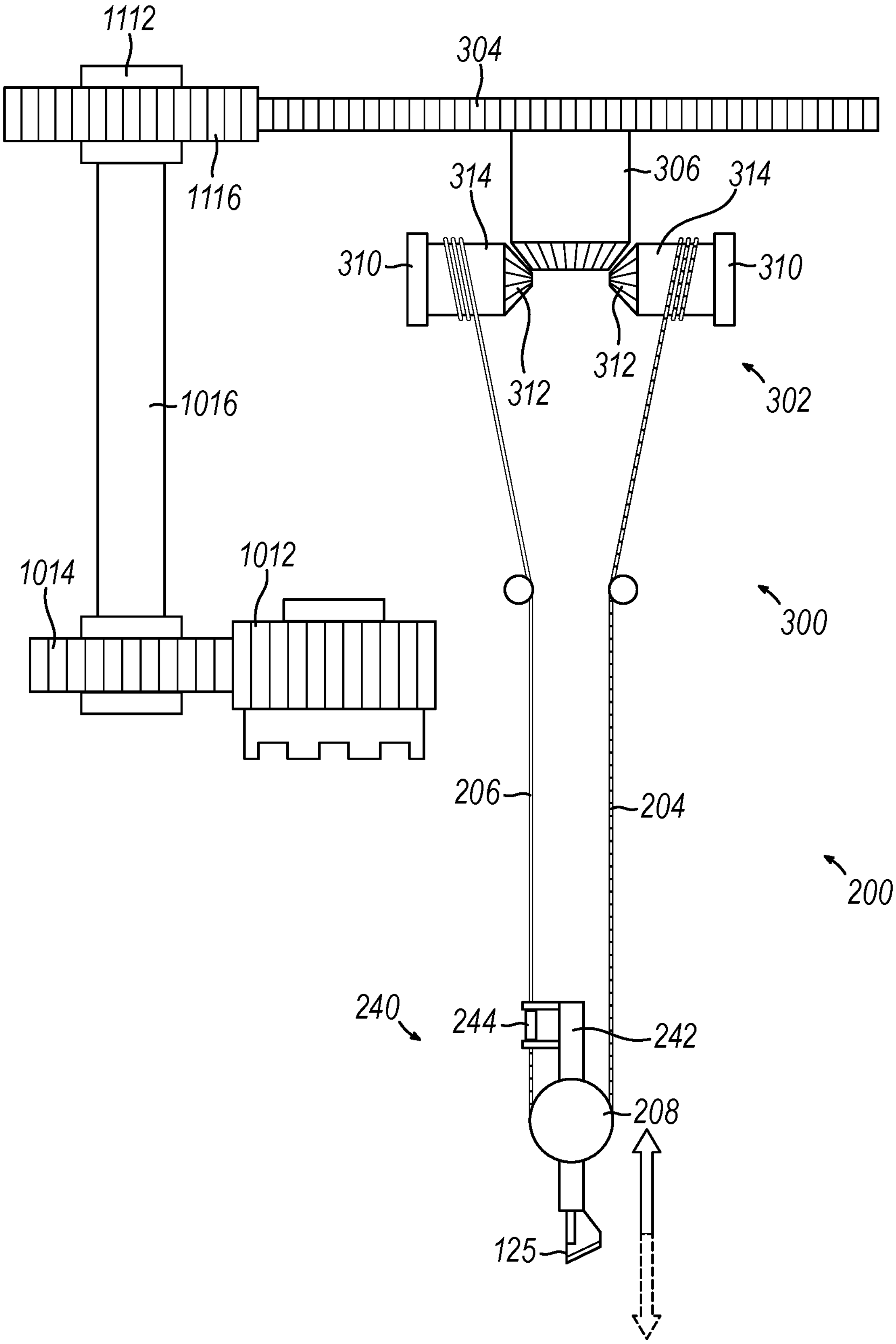
FIG. 22 depicts a top plan view of an alternative knife driving assembly.

FIG. 22 shows an alternative knife driving assembly (300) that may be incorporated to replace knife driving assembly (200, 260, 280) described above. Therefore, knife driving assembly (300) may be substantially similar to knife driving assembly (200, 260, 280) described above, with differences elaborated below. Driving assembly (300) includes a drive input assembly (302) operatively coupled to distal portion (240) via cable (202).

Portions (204, 206) of cable (202) are operatively coupled to a respective cable feed body (314) of a cable feed assembly (310). Each cable feed assembly (310) in the current example is rotated via a plurality of gears (304, 306) that are driven by gear (1116) such that a single drive input (1012) may rotate gears (304, 306) in a first angular direction and a second, opposite, angular direction in accordance with the description herein. Each cable feed assembly (310) includes a bevel gear (312) that engages bevel gear (306).

Rotation of cable feed body (314) in a first angular direction feeds cable (202) away from body (314), while rotation of cable feed body (314) in a second, opposite, angular direction spools/receives cable (202). Each portion (204, 206) is coupled to a similar cable feed body (314); however, cable feed bodies (314) are engaged with a first bevel gear (306) such that rotation of bevel gear (306) in a single angular direction rotates each cable feed body (314) in opposite angular directions relative to each other. Therefore, First bevel gear (306) may rotate in a first angular direction to simultaneously drive portion (206) of cable (202) distally and portion (204) of cable (202) proximally, thereby firing knife member (125); and then rotate in a second, opposite, angular direction to simultaneously spool portion (206) of cable proximally and drive portion (204) of cable (202) distally, thereby retracting knife member (125). Gears (304, 306) and cable feed assemblies (310) may be rotationally supported by suitable features as would be apparent to one skilled in the art in view of the teachings herein.

Figure 23:
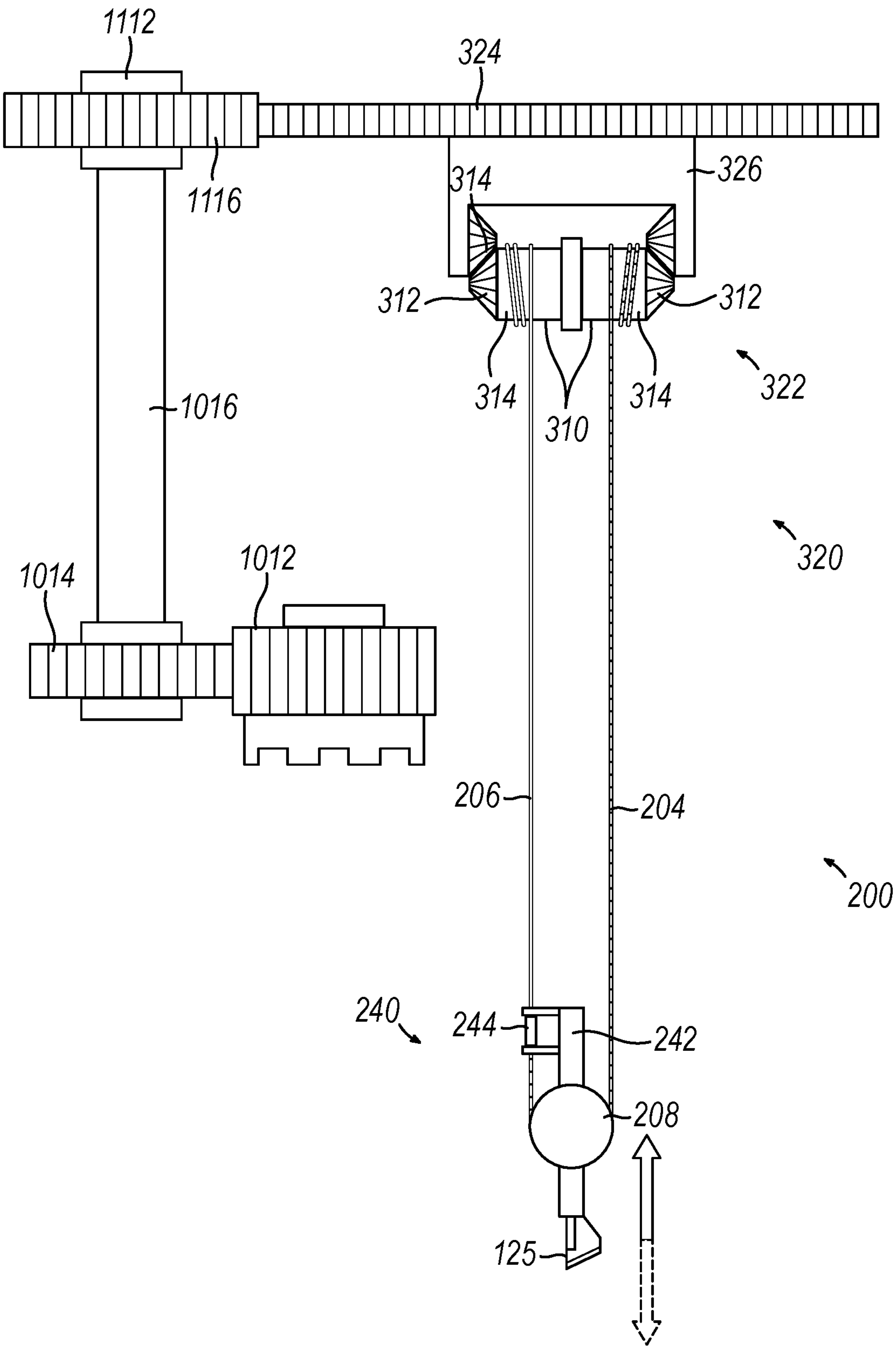
FIG. 23 depicts a top plan view of an alternative knife driving assembly.

FIG. 23 shows an alternative knife driving assembly (320) that may be incorporated to replace knife driving assembly (200, 260, 280, 300) described above. Therefore, knife driving assembly (320) may be substantially similar to knife driving assembly (200, 260, 280, 300) described above, with differences elaborated below. Driving assembly (320) includes a drive input assembly (322) operatively coupled to distal portion (240) via cable (202).

Drive input assembly (322) includes cable feed assemblies (310) described above but oriented differently in order to suitably engage an internal bevel gear (326) operatively coupled to gear (324), rather than bevel gear (306) shown in FIG. 22. Internal bevel gear (326) is attached to gear (324). Gears (324, 326) are driven by gear (1116) such that a single drive input (1012) may rotate gears (324, 326) in a first angular direction and a second, opposite, angular direction in accordance with the description herein. Therefore, internal bevel gear (326) may rotate each cable feed assembly (310) in opposing direction simultaneously in order to advance and retract knife member (125) in accordance with the description herein. Gears (324, 326) and cable feed assemblies (310) may be rotationally supported by suitable features as would be apparent to one skilled in the art in view of the teachings herein.

Figure 24:
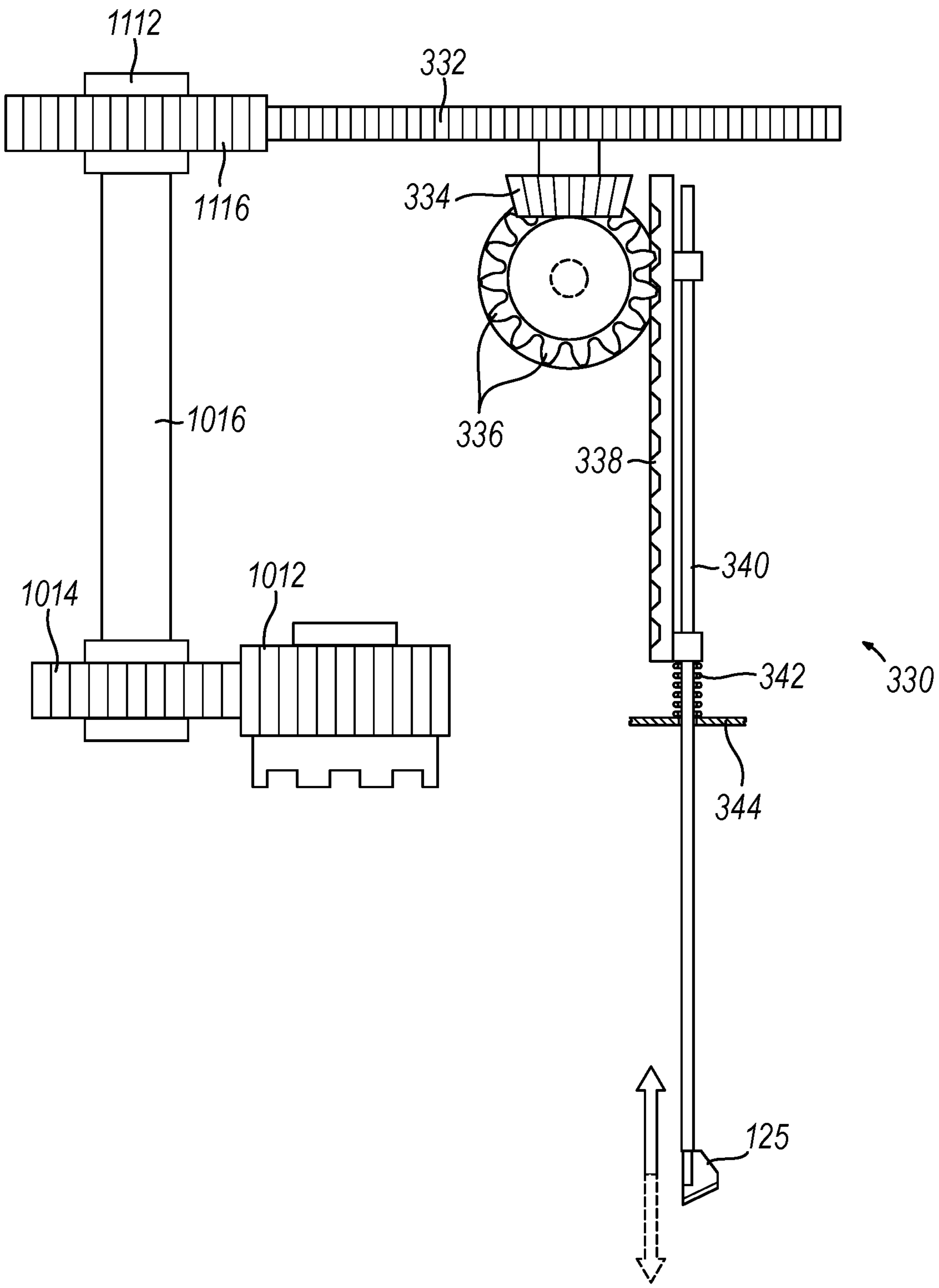
FIG. 24 depicts a top plan view of an alternative knife driving assembly.

FIG. 24 shows an alternative knife driving assembly (330) that may be incorporated to replace knife driving assembly (200, 260, 280, 300, 320) described above. Therefore, knife driving assembly (330) may be substantially similar to knife driving assembly (200, 260, 280, 300, 320) described above, with differences elaborated below.

In the current example, knife driving assembly (330) does not include a cable coupled to knife member (125). Instead, knife member (125) is attached to an elongated driving body (340) configured to drive knife member (125) between the proximal and distal positions in accordance with the description herein.

Knife drive assembly (330) includes a first gear (332) fixed a bevel gear (334), which is operatively engaged with a spur gear (336). Bevel gear (334) is configured to rotate spur gears (336). Spur gear (336) is engaged with a rack (338) that is fixed to elongated riving body (340). Elongated driving body (340) is biased toward the proximal position via a spring (342) interposed between driving body (340) and a mechanical ground (344) associated with drive chassis (134). Gears (332, 334, 336) are driven by gear (1116) such that a single drive input (1012) may rotate gears (332, 334, 336) in a first angular direction and a second, opposite, angular direction in accordance with the description herein.

In order to fire knife member (125) distally, gears (332, 334, 336) are rotated in a first angular direction, thereby driving rack (338) and elongated driving body (340) distally. Conversely, in order to retract knife member (125) proximally, gears (332, 334, 336) are rotated in a second angulate direction, thereby driving rack (338) and elongated driving body (340) proximally. Gears (332, 334, 336) may be rotationally supported by suitable features as would be apparent to one skilled in the art in view of the teachings herein.

Figure 25:
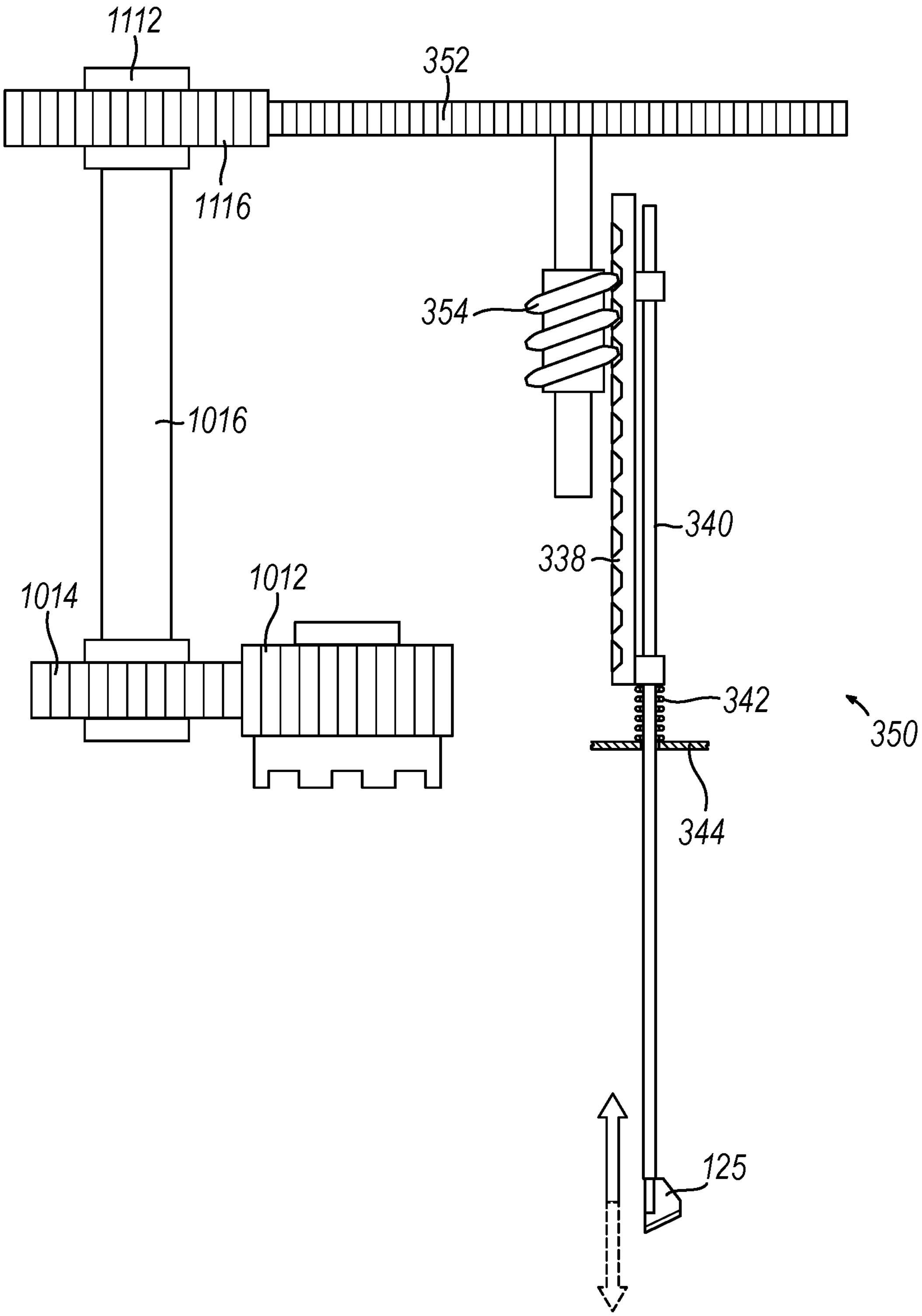
FIG. 25 depicts a top plan view of an alternative knife driving assembly.

FIG. 25 shows an alternative knife driving assembly (350) that may be incorporated to replace knife driving assembly (200, 260, 280, 300, 320, 330) described above. Knife driving assembly (350) may be substantially similar to knife driving assembly (330) described above, except, rather than using a spur gears (336) and a bevel gear (334) to generate translation of rack (338), rack (338) is engaged with a worm gear (354) that is fixed to gear (352). Worm gear (354) may rotate in order to distally advance and proximally retract knife member (125) in accordance with the description herein. Gears (352, 354) are driven by gear (1116) such that a single drive input (1012) may rotate gears (352, 354) in a first angular direction and a second, opposite, angular direction in accordance with the description herein. Gears (352, 354) may be rotationally supported by suitable features as would be apparent to one skilled in the art in view of the teachings herein.

Figure 26:
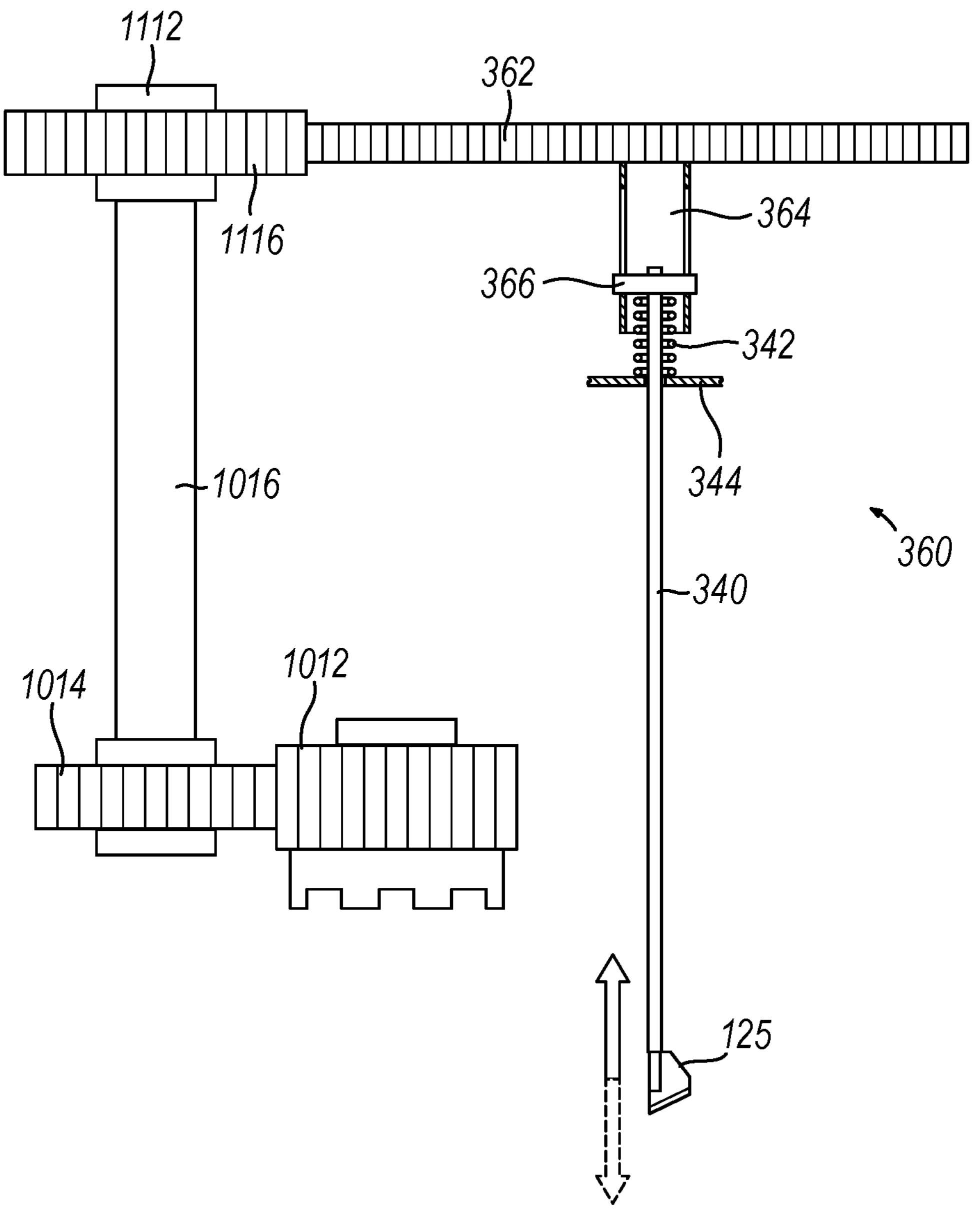
FIG. 26 depicts a top plan view of an alternative knife driving assembly.
Figure 27:
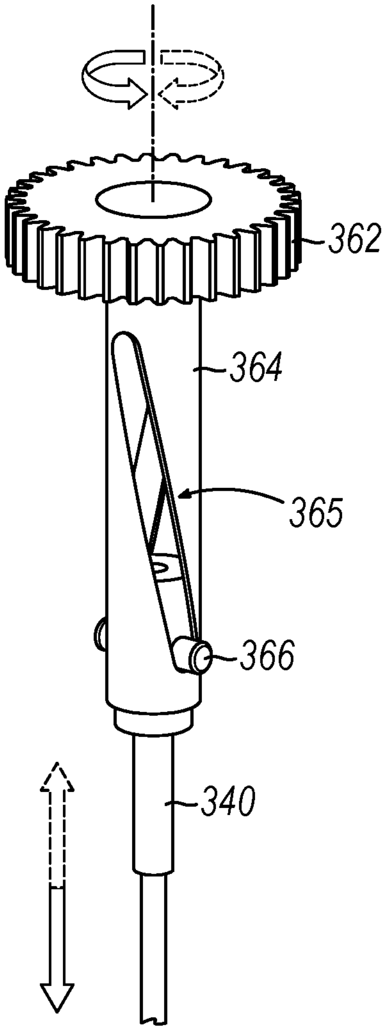
FIG. 27 depicts a perspective view of a gear and a hollow body configured to drive translation of the alternative knife driving assembly of FIG. 26.

FIGS. 26-27 show an alternative knife driving assembly (360) that may be incorporated to replace knife driving assembly (200, 260, 280, 300, 320, 330, 350) described above. Knife driving assembly (360) may be substantially similar to knife driving assembly (330, 350) described above, except, rather than using a rack (338) to drive translation of knife member (125), knife driving assembly (360) uses a hollow body (364) defining helical cam slots (365) to proximal and distal translate a driving pin (366) fixed to elongated body (340). Drive pin (366) is rotationally fixed relative to mechanical ground (344), but translatable relative to mechanical ground (334). Gear (362) is driven by gear (1116) such that a single drive input (1012) may rotate gear (362) in a first angular direction and a second, opposite, angular direction in accordance with the description herein.

Rotation of gear (362) and hollow body (364) in a first angular direction allows cam slots (365) to drive pin (366), elongated body (340), and knife member (125) distally; while rotation of gear (362) in the second, opposite, angular direction allows cam slots (365) to drive pin (366), elongated body (340), and knife member (125) proximally. Gear (362) and hollow body (364) may be rotationally supported by suitable features as would be apparent to one skilled in the art in view of the teachings herein.

Figure 28:
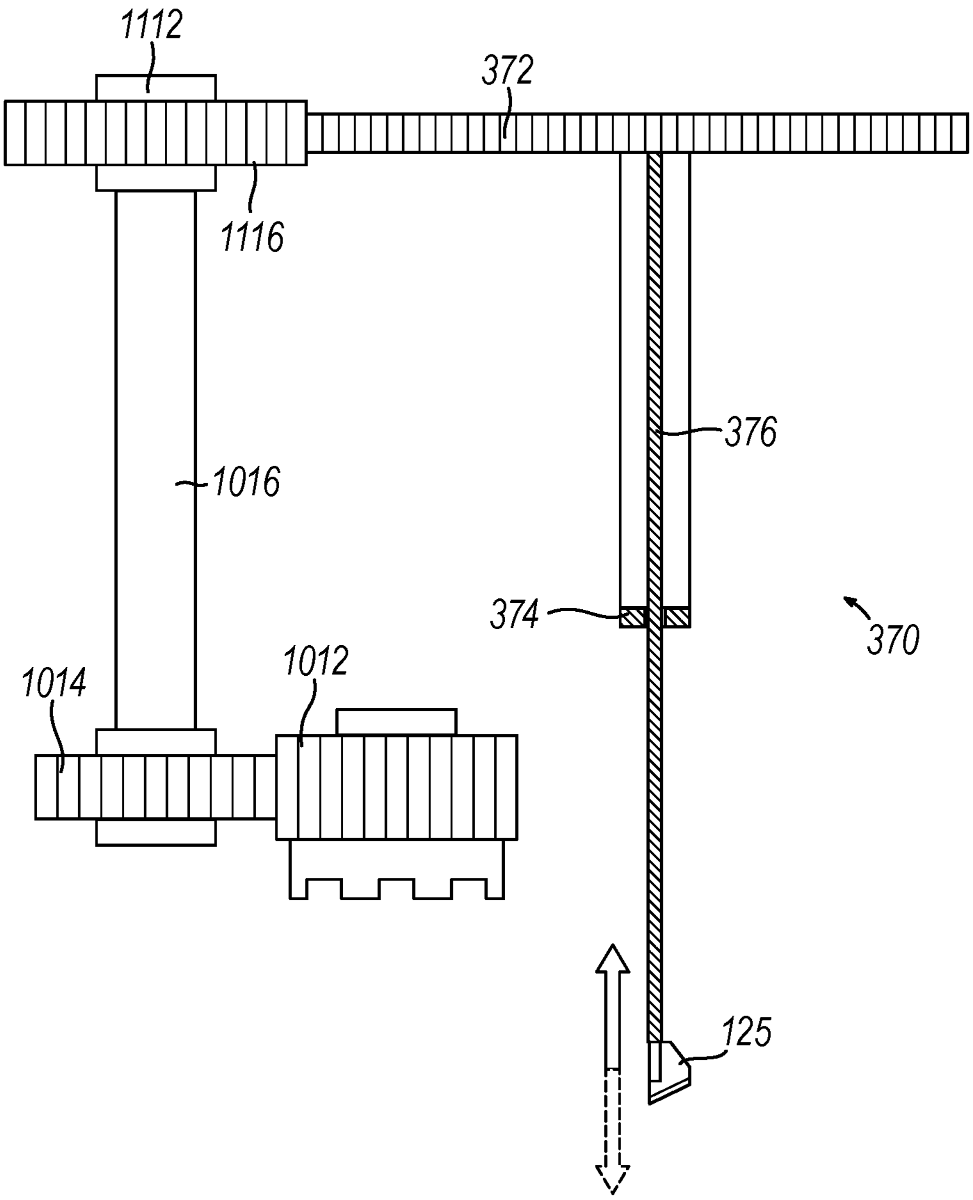
FIG. 28 depicts a top plan view of an alternative knife driving assembly.

FIG. 28 shows an alternative knife driving assembly (370) that may be incorporated to replace knife driving assembly (200, 260, 280, 300, 320, 330, 350, 360) described above. Knife driving assembly (370) may be substantially similar to knife driving assembly (360) described above, except rather than using cam slot (365), knife drive member (370) includes a hollow body having a threading (374) configured to rotate in order to translate a threaded elongated body (376) attached to knife member (125). Hollow body having a threading (374) is attached to gear (372). Gear (372) is driven by gear (1116) such that a single drive input (1012) may rotate gear (372) in a first angular direction and a second, opposite, angular direction in accordance with the description herein.

Threaded elongated body (376) is rotationally fixed, but translatable, relative to gear (372) and hollow body having a threading (374). Therefore, hollow body having threading (374) engages threaded elongated body (376) such that rotation of gear (372) drives translation of threaded body (376) to advance and retract knife member (125) in accordance with the description herein.

Figure 29:
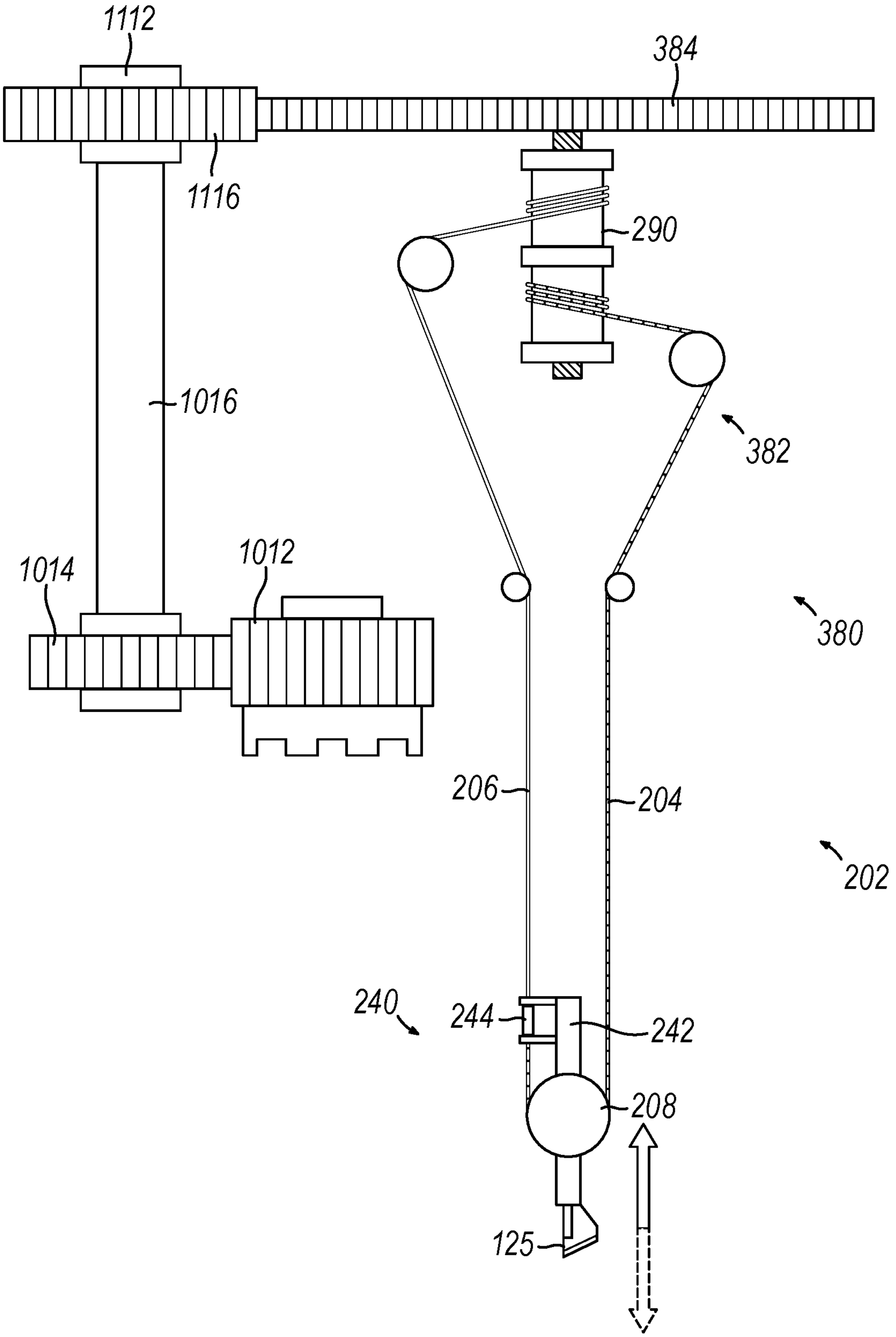
FIG. 29 depicts a top plan view of an alternative knife driving assembly.

FIG. 29 shows an alternative knife driving assembly (380) that may be incorporated to replace knife driving assembly (200, 260, 280, 300, 320, 330, 350, 360, 370) described above. Therefore, knife driving assembly (380) may be substantially similar to knife driving assembly (200, 260, 280, 300, 320, 330, 350, 360, 370) described above, with differences elaborated below. Driving assembly (380) includes a drive input assembly (382) operatively coupled to distal portion (240) via cable (202).

Portions (204, 206) of cable (202) are operatively coupled to a dual threaded cable feed assembly (290) that is configured to simultaneously feed a first portion (204, 206) of cable (202) away from cable feed assembly (290) while spooling/receiving the opposite portion (204, 206) of cable (202) in response to rotation in a single angular direction. Therefore, rotation of cable feed assembly (290) in a first angular direction distally advance knife member (125), while rotation of cable feed assembly (290) in a second, opposite, angular direction proximally retracted knife member (125).

However, dual threaded cable feed assembly (290) in the current example is rotated via gear (384) that is driven by gear (1116) such that a single drive input (1012) may rotate gear (384) in a first angular direction and a second, opposite, angular direction in accordance with the description herein. Gear (384) is directly coupled cable feed assembly (290) in order to suitably rotate cable feed assembly (290). Therefore, Gear (384) may be rotated in a first angular direction and a second angular direction in order to drive knife member (125) distally and proximally in accordance with the description herein. Gear (384) and cable feed assembly (290) may be rotationally supported by suitable features as would be apparent to one skilled in the art in view of the teachings herein.

IV. Illustrative Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) an end effector, the end effector comprising: (i) a pair of jaws configured to actuate between an open configuration and a closed configuration, and (ii) a knife member configured to actuate between a proximal position and a distal position while the pair of jaws are in the closed configuration; (b) a shaft assembly extending proximally from the end effector; (c) an instrument base attached to the shaft assembly, wherein the instrument base comprises at least one drive input; and (d) a knife driving assembly configured to actuate the knife member between the proximal position and the distal position, wherein the knife driving assembly comprises: (i) a knife drive input assembly coupled to only a first drive input of the at least one drive input, wherein the knife drive input assembly is configured to rotate in a first angular direction and a second angular direction, (ii) a cable terminating into a first end and a second end, wherein both the first end and the second end are attached to the knife drive input assembly, wherein a portion of the cable is attached to the knife member, wherein rotation of the knife drive input assembly in the first angular direction is configured to drive the knife member toward the distal position, wherein rotation of the knife drive input assembly in the second angular direction drives the knife member toward the proximal position.

Example 2

The apparatus of any one or more of the preceding Examples, wherein the knife driving assembly further comprises a distal pulley associated with either the shaft assembly or the end effector, wherein the cable loops around the distal pulley.

Example 3

The apparatus of any one or more of the preceding Examples, wherein the knife drive input assembly comprises a ring gear having a plurality of external teeth.

Example 4

The apparatus of any one or more of the preceding Examples, wherein ring gear comprise a pair of internal teeth, wherein the knife drive input assembly comprises a first capstan coupled to the first end of the cable and a second capstan coupled to the second end of the cable, wherein the internal teeth are configured to rotate both the first capstan and the second capstan in the same angular direction.

Example 5

The apparatus of any one or more of the preceding Examples, wherein the first capstan comprises a first internal gear, wherein the second capstan comprises a second internal gear.

Example 6

The apparatus of any one or more of the preceding Examples, wherein the knife drive input comprises a dual threaded cable feed assembly.

Example 7

The apparatus of any one or more of the preceding Examples, wherein the dual threaded cable feed assembly further comprises a gear.

Example 8

The apparatus of any one or more of the preceding Examples, wherein the knife drive input comprises a first bevel gear attached to the dual threaded cable feed assembly.

Example 9

The apparatus of any one or more of the preceding Examples, wherein the knife drive input comprises a second bevel gear operatively engaged with the first bevel gear.

Example 10

The apparatus of any one or more of the preceding Examples, wherein the first bevel gear comprises a hollow opening receiving the dual threaded cable feed assembly.

Example 11

The apparatus of any one or more of the preceding Examples, wherein the instrument base comprises an elongated spline shaft.

Example 12

The apparatus of any one or more of the preceding Examples, wherein the instrument base comprises a threaded rod.

Example 13

The apparatus of any one or more of the preceding Examples, wherein the threaded rod is configured to drive the shaft assembly relative to the instrument base.

Example 14

The apparatus of any one or more of the preceding Examples, wherein the elongated spline shaft is configured to rotate the knife driving assembly.

Example 15

The apparatus of any one or more of the preceding Examples, wherein the knife driving assembly is slidably attached to the elongated spline shaft.

Example 16

An apparatus, comprising: (a) an end effector comprising a knife member configured to actuate between a proximal position and a distal position; (b) a shaft assembly extending proximally from the end effector; (c) an instrument base attached to the shaft assembly, wherein the instrument base comprises at least one drive input; and (d) a knife driving assembly configured to actuate the knife member between the proximal position and the distal position, wherein the knife driving assembly comprises: (i) a knife drive input assembly coupled to only a first drive input of the at least one drive input, wherein the knife driving assembly comprises: (A) a ring gear is configured to rotate in a first angular direction and a second angular direction, (B) a first capstan, and (C) a second capstan, wherein the first capstan and the second capstan are configured to simultaneously rotate in response to rotation of the ring gear; and (ii) a cable terminating into a first end and a second end, wherein the first end is attached to the first capstan, wherein the second end is attached to the second capstan, wherein a portion of the cable is attached to the knife member, wherein rotation of the ring gear in the first angular direction is configured to drive the knife member toward the distal position, wherein rotation of the ring gear in the second angular direction drives the knife member toward the proximal position.

Example 17

The apparatus of any one or more of the preceding Examples, wherein the instrument base slidably receives the shaft assembly.

Example 18

The apparatus of any one or more of the preceding Examples, wherein the end effector is configured to articulate relative to the shaft assembly.

Example 19

The apparatus of any one or more of the preceding Examples, wherein the ring gear comprise an inner array of teeth and an outer array of teeth.

Example 20

An apparatus, comprising: (a) an end effector, the end effector comprising: (i) a pair of jaws configured to actuate between an open configuration and a closed configuration, and (ii) a knife member configured to actuate between a proximal position and a distal position while the pair of jaws are in the closed configuration; (b) an instrument base located proximally relative to the end effector wherein the instrument base comprises at least one drive input; and (c) a knife driving assembly configured to actuate the knife member between the proximal position and the distal position, wherein the knife driving assembly comprises a knife drive input assembly attached to the instrument base, wherein the knife drive input assembly is coupled to only a first drive input of the at least one drive input, wherein the knife driving assembly is configured to rotate in a first angular direction and a second angular direction to thereby drive the knife member toward the proximal position and the distal position, respectively.

V. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:

(a) an end effector, the end effector comprising:
  (i) a pair of jaws configured to acuate between an open configuration and a closed configuration, and
  (ii) a knife member configured to acuate between a proximal position and a distal position while the pair of jaws are in the closed configuration;

(b) a shaft assembly extending proximally from the end effector;

(c) an instrument base attached to the shaft assembly, wherein the instrument base comprises an elongated spline shaft and at least one drive input; and (d) a knife driving assembly configured to actuate the knife member between the proximal position and the distal position, wherein the knife driving assembly comprises:
  (i) a knife drive input assembly coupled to only a first drive input of the at least one drive input, wherein the knife drive input assembly is configured to rotate in a first angular direction and a second angular direction,
  (ii) a cable terminating into a first end and a second end, wherein both the first end and the second end are attached to the knife drive input assembly, wherein a portion of the cable is attached to the knife member, wherein rotation of the knife drive input assembly in the first angular direction is configured to drive the knife member toward the distal position, wherein rotation of the knife drive input assembly in the second angular direction drives the knife member toward the proximal position.

2. The apparatus of claim 1, wherein the knife driving assembly further comprises a distal pulley associated with either the shaft assembly or the end effector, wherein the cable loops around the distal pulley.

3. The apparatus of claim 2, wherein the knife drive input assembly comprises a ring gear having a plurality of external teeth.

4. The apparatus of claim 1, wherein the knife drive input comprises a dual threaded cable feed assembly.

5. The apparatus of claim 4, wherein the dual threaded cable feed assembly further comprises a gear.

6. The apparatus of claim 4, wherein the knife drive input comprises a first bevel gear attached to the dual threaded cable feed assembly.

7. The apparatus of claim 6, wherein the knife drive input comprises a second bevel gear operatively engaged with the first bevel gear.

8. The apparatus of claim 6, wherein the first bevel gear comprises a hollow opening receiving the dual threaded cable feed assembly.

9. The apparatus of claim 1, wherein the instrument base comprises a threaded rod.

10. The apparatus of claim 9, wherein the threaded rod is configured to drive the shaft assembly relative to the instrument base.

11. The apparatus of claim 1, wherein the elongated spline shaft is configured to rotate the knife driving assembly.

12. The apparatus of claim 11, wherein the knife driving assembly is slidably attached to the elongated spline shaft.

13. An apparatus, comprising:

(a) an end effector comprising a knife member configured to acuate between a proximal position and a distal position;

(b) a shaft assembly extending proximally from the end effector;

(c) an instrument base attached to the shaft assembly, wherein the instrument base comprises at least one drive input; and (d) a knife driving assembly configured to actuate the knife member between the proximal position and the distal position, wherein the knife driving assembly comprises:
  (i) a knife drive input assembly coupled to only a first drive input of the at least one drive input, wherein the knife driving assembly comprises:
    (A) a ring gear is configured to rotate in a first angular direction and a second angular direction,
    (B) a first capstan, and
    (C) a second capstan, wherein the first capstan and the second capstan are configured to simultaneously rotate in response to rotation of the ring gear; and
  (ii) a cable terminating into a first end and a second end, wherein the first end is attached to the first capstan, wherein the second end is attached to the second capstan, wherein a portion of the cable is attached to the knife member, wherein rotation of the ring gear in the first angular direction is configured to drive the knife member toward the distal position, wherein rotation of the ring gear in the second angular direction drives the knife member toward the proximal position.

14. The apparatus of claim 13, wherein the instrument base slidably receives the shaft assembly.

15. The apparatus of claim 13, wherein the end effector is configured to articulate relative to the shaft assembly.

16. The apparatus of claim 13, wherein the ring gear comprise an inner array of teeth and an outer array of teeth.

17. An apparatus, comprising:

(a) an end effector, the end effector comprising:

(i) a pair of jaws configured to acuate between an open configuration and a closed configuration, and (ii) a knife member configured to acuate between a proximal position and a distal position while the pair of jaws are in the closed configuration;

(b) a shaft assembly extending proximally from the end effector;

(c) an instrument base attached to the shaft assembly, wherein the instrument base comprises at least one drive input; and (d) a knife driving assembly configured to actuate the knife member between the proximal position and the distal position, wherein the knife driving assembly comprises:

(i) a knife drive input assembly coupled to only a first drive input of the at least one drive input, wherein the knife drive input assembly is configured to rotate in a first angular direction and a second angular direction, and wherein the knife drive input assembly includes a ring gear having a plurality of external teeth, (ii) a cable terminating into a first end and a second end, wherein both the first end and the second end are attached to the knife drive input assembly, wherein a portion of the cable is attached to the knife member, wherein rotation of the knife drive input assembly in the first angular direction is configured to drive the knife member toward the distal position, wherein rotation of the knife drive input assembly in the second angular direction drives the knife member toward the proximal position.

18. The apparatus of claim 17, wherein the knife driving assembly further comprises a distal pulley associated with either the shaft assembly or the end effector, wherein the cable loops around the distal pulley.

19. The apparatus of claim 18, wherein ring gear comprise a pair of internal teeth, wherein the knife drive input assembly comprises a first capstan coupled to the first end of the cable and a second capstan coupled to the second end of the cable, wherein the internal teeth are configured to rotate both the first capstan and the second capstan in the same angular direction.

20. The apparatus of claim 19, wherein the first capstan comprises a first internal gear, wherein the second capstan comprises a second internal gear.

* * * * *